US012766226B2

(12) United States Patent
Tsumaki

(10) Patent No.: US 12,766,226 B2
(45) Date of Patent: Oct. 20, 2026

(54) PLURIPOTENT STEM CELL-DERIVED PLATE-SHAPED CARTILAGE AND METHOD FOR PRODUCING THE SAME

(71) Applicant: KYOTO UNIVERSITY, Kyoto (JP)

(72) Inventor: Noriyuki Tsumaki, Kyoto (JP)

(73) Assignee: KYOTO UNIVERSITY, Kyoto (JP)

(*) Notice: Subject to any disclaimer, the term of this patent is extended or adjusted under 35 U.S.C. 154(b) by 935 days.

(21) Appl. No.: 17/260,443

(22) PCT Filed: Jul. 18, 2019

(86) PCT No.: PCT/JP2019/028193
§ 371 (c)(1),
(2) Date: Jan. 14, 2021

(87) PCT Pub. No.: WO2020/017575
PCT Pub. Date: Jan. 23, 2020

(65) Prior Publication Data

US 2021/0299331 A1 Sep. 30, 2021

Related U.S. Application Data

(60) Provisional application No. 62/700,489, filed on Jul. 19, 2018.

(51) Int. Cl.

| | |
|---|---|
| ***A61L 27/38*** | (2006.01) |
| ***A61F 2/46*** | (2006.01) |
| ***C12N 5/077*** | (2010.01) |

(52) U.S. Cl.
CPC ........ *A61L 27/3852* (2013.01); *A61F 2/4618* (2013.01); *C12N 5/0655* (2013.01); *C12N 2501/119* (2013.01)

(58) Field of Classification Search
CPC . A61L 27/3852; A61F 2/4618; C12N 5/0655; C12N 2501/119
See application file for complete search history.

(56) References Cited

U.S. PATENT DOCUMENTS

| | | | | |
|---|---|---|---|---|
| 6,242,247 | B1 | 6/2001 | Rieser et al. | |
| 7,022,518 | B1 * | 4/2006 | Feye | C12M 25/14 435/297.1 |
| 10,557,121 | B2 * | 2/2020 | Tsumaki | A61P 19/04 |
| 2001/0014473 | A1 | 8/2001 | Rieser et al. | |
| 2014/0349330 | A1 | 11/2014 | Fayol et al. | |
| 2016/0251623 | A1 | 9/2016 | Tsumaki | |
| 2018/0251732 | A1 * | 9/2018 | Tsumaki | A61L 27/3817 |

FOREIGN PATENT DOCUMENTS

| | | | | |
|---|---|---|---|---|
| JP | 2000-513214 A | | 10/2000 | |
| JP | 2014-525256 A | | 9/2014 | |
| WO | WO 2015/064754 A1 | | 5/2015 | |
| WO | WO 2016/1332208 | * | 8/2016 | |
| WO | WO-2016133208 A1 | * | 8/2016 | A61K 35/32 |
| WO | WO 2018/009147 A1 | | 1/2018 | |

OTHER PUBLICATIONS

Pacifici, Maurizio, Eiki Koyama, and Masahiro Iwamoto. "Mechanisms of synovial joint and articular cartilage formation: recent advances, but many lingering mysteries." Birth Defects Research Part C: Embryo Today: Reviews 75.3: 237-248. (Year: 2006).*
Correa, Diego, et al. "Sequential exposure to fibroblast growth factors (FGF) 2, 9 and 18 enhances hMSC chondrogenic differentiation." Osteoarthritis and Cartilage 23.3: 443-453. (Year: 2015).*
Sennett, Mackenzie L., et al. "Sprifermin treatment enhances cartilage integration in an in vitro repair model." Journal of Orthopaedic Research® 36.10 (2018): 2648-2656. (Year: 2018).*
Zhang, Zhenyu, et al. "Fibroblast growth factor 18 increases the trophic effects of bone marrow mesenchymal stem cells on chondrocytes isolated from late stage osteoarthritic patients." Stem Cells International 2014.1 (2014): 125683. (Year: 2014).*
Gilbert, Eric, et al. "A novel through-thickness perfusion bioreactor for the generation of scaffold-free tissue engineered cartilage." Processes 2.3 (2014): 658-674. (Year: 2014).*
Extended European Search Report for European Application No. 19837466.2, dated Mar. 21, 2022.
Chen et al., "Integration Capacity of Human Induced Pluripotent Stem Cell-Derived Cartilage", Tissue Engineering: Part A, vol. 25, No. 5-6, 2019, pp. 437-445.
Correa et al., "Sequential exposure to fibroblast growth factors (FGF) 2, 9 and 18 enhances hMSC chondrogenic differentiation", Osteoarthritis and Cartilage, vol. 23, 2015, pp. 443-453.
Davidson et al., "Fibroblast Growth Factor (FGF) 18 Signals through FGF Receptor 3 to Promote Chondrogenesis", The Journal of Biological Chemistry, vol. 280, No. 21, May 27, 2005, pp. 20509-20515.
Huang et al., "Synergistic Effects of FGF-18 and TGF-β3 on the Chondrogenesis of Human Adipose-Derived Mesenchymal Stem Cells in the Pellet Culture", Stem Cells International, vol. 2018, 2018, pp. 1-10.

(Continued)

*Primary Examiner* — Teresa E Knight
*Assistant Examiner* — Michael Angelo Riga
(74) *Attorney, Agent, or Firm* — Birch, Stewart, Kolasch & Birch, LLP

(57) ABSTRACT

Provided is a plate-shaped cartilage comprising a plurality of pluripotent stem cell-derived cartilaginous particles integrated with one another; and a method for producing the plate-shaped cartilage, comprising step 1: producing pluripotent stem cell-derived cartilaginous particles, and step 2: culturing the cartilaginous particles under culture conditions that allow adjacent cartilaginous particles to be in contact with one another, wherein the number of the cartilaginous particles is that amount required to form the plate-shaped cartilage.

2 Claims, 9 Drawing Sheets

Specification includes a Sequence Listing.

(56) References Cited

OTHER PUBLICATIONS

International Search Report issued in PCT/JP2019/028193 (PCT/ISA/210), dated Sep. 24, 2019.

Kimura et al., "Limited Immunogenicity of Human Induced Pluripotent Stem Cell-Derived Cartilages", Tissue Engineering: Part A, Nature, vol. 22, No. 23-24, 2016, pp. 1367-1375.

Written Opinion of the International Searching Authority issued in PCT/JP2019/028193 (PCT/ISA/237), dated Sep. 24, 2019.

Yamashita et al., "Generation of Scaffoldless Hyaline Cartilaginous Tissue from Human iPSCs", Stem Cell Reports, vol. 4, Mar. 10, 2015, pp. 404-418.

Yamashita et al., "Statin treatment rescues FGFR3 skeletal dysplasia phenotypes", vol. 513, Nature, Sep. 25, 2014, pp. 507-523.

International Preliminary Report on Patentability and English translation of the Written Opinion of the International Searching Authority for International Application No. PCT/JP2019/028193, dated Jan. 28, 2021.

European Communication pursuant to Article 94(3) EPC for European Application No. 19 837 466.2, dated Jul. 2, 2025.

* cited by examiner

** : P<0.01 compared with central cartilage by Student's t-test (n=3 technical replicates)

PLURIPOTENT STEM CELL-DERIVED PLATE-SHAPED CARTILAGE AND METHOD FOR PRODUCING THE SAME

CROSS REFERENCE TO RELATED APPLICATIONS

This application is the National Phase of PCT International Application No. PCT/JP2019/028193, filed on Jul. 18, 2019, which claims priority under 35 U.S.C. 119 (e) to U.S. Provisional Application No. 62/700,489, filed on Jul. 19, 2018, all of which are hereby expressly incorporated by reference into the present application.

TECHNICAL FIELD

The present invention relates to a pluripotent stem cell-derived plate-shaped cartilage and a method for producing the same.

BACKGROUND ART

Articular cartilage covers the ends of bones and provides lubrication between opposing bones during joint motion. Articular cartilage consists of chondrocytes and cartilage extracellular matrix (ECM), which embeds chondrocytes. Chondrocytes produce cartilage ECM, while cartilage ECM provides chondrocytes with an environment that supports chondrocytes to sustain chondrocytic properties including cartilage ECM production, indicating that chondrocytes and cartilage ECM have a mutually dependent relationship.

Cartilage injury rarely heals spontaneously due to a loss of cartilage ECM. New chondrocytes are not generated in the absence of cartilage ECM, and non-chondrocytic cells do not produce cartilage ECM in joint surface defects generated by the injury. As a cartilage regenerative therapy, implantation of autologous chondrocytes or mesenchymal stem cells to an articular cartilage defect site has recently been employed, but cell implantation without cartilage ECM do not result in cartilage regeneration, as indicated by the formation of fibrocartilaginous repair tissue. In order to overcome this limitation, allogeneic cartilage implantation has been employed. For treatment of articular cartilage injury, allogeneic cartilage is transplanted without matching HLA types or use of immunosuppressive drugs because cartilage has low immunogenicity. To date, promising results have been obtained, but several concerns remain, including the lack of donors, the heterogeneity in the quality of the cartilages obtained from different individuals, and the risk of disease transmission. Therefore, there is a demand for an alternative method. In particular, new materials that can be used for transplantation to an articular cartilage defect site in regenerative therapy for joint injury are desired.

The present inventor and others previously reported a method for generating scaffoldless cartilage tissues from human iPS cells (Patent Literature 1 and 2, and Non Patent Literature 1 and 2). Three-dimensional culture of chondrogenically-differentiated human iPS cells in suspension culture induces secretion and deposition of cartilage ECM, leading to cartilage formation. The obtained human iPS cell-derived cartilage (hereinafter referred to as human iPS cell-derived cartilaginous particles) is spherical and has a diameter of about 1 to 3 mm. Human iPS cell-derived cartilaginous particles transplanted to an articular cartilage defect site in immunosuppressed mini-pigs formed articular cartilage, which showed indications of integration with mini-pig native articular cartilage at 4 weeks after transplantation (Non Patent Literature 1). Human iPS cell-derived cartilaginous particles transplanted to an articular cartilage defect in immunodeficient rats were integrated with adjacent rat native cartilage at the sides and with bone at the bottom at 4 weeks after transplantation (Non Patent Literature 1). In addition, the present inventor and others found that human iPS cell-derived cartilaginous particles have low immunogenicity like natural cartilage, as indicated by the lack of proliferation of lymphocytes in a mixed lymphocyte reaction assay (Non Patent Literature 3). These findings collectively suggest that human iPS cell-derived cartilaginous particles can be a new source for allogeneic transplantation to treat articular cartilage defects. The number of human iPS cell-derived cartilaginous particles needed to fill a defect site depends on the size of the defect site in the articular cartilage. In clinical settings, the present inventor and others are planning to implant around 25 human iPS cell-derived cartilaginous particles per 1 $cm^2$ defect site and fix them with fibrin glue. However, fibrin glue fixation of a plurality of cartilaginous particles is weak, which may result in falling out of cartilaginous particles after transplantation.

The present inventor and others reported that two human iPS cell-derived cartilaginous particles obtained at 90 days after the start of differentiation were cultured in contact with each other in culture medium for 60 days, resulting in integration of the two particles into one larger particle (Patent Literature 1).

CITATION LIST

Patent Literature

Patent Literature 1: WO 2015/064754

Patent Literature 2: WO 2016/133208

Non Patent Literature

Non Patent Literature 1:

Yamashita, A., Morioka, M., Yahara, Y., Okada, M., Kobayashi, T., Kuriyama, S., Matsuda, S., and Tsumaki, N. Generation of Scaffoldless Hyaline Cartilaginous Tissue from Human iPSCs. Stem cell reports 4, 404, 2015.

Non Patent Literature 2:

Yamashita, A., Morioka, M., Kishi, H., Kimura, T., Yahara, Y., Okada, M., Fujita, K., Sawai, H., Ikegawa, S., and Tsumaki, N. Statin treatment rescues FGFR3 skeletal dysplasia phenotypes. Nature 513, 507, 2014.

Non Patent Literature 3:

Kimura, T., Yamashita, A., Ozono, K., and Tsumaki, N. Limited Immunogenicity of Human Induced Pluripotent Stem Cell-Derived Cartilages. Tissue Eng Part A 22, 1367, 2016.

SUMMARY OF INVENTION

Technical Problem

An object of the present invention is to provide a pluripotent stem cell-derived plate-shaped cartilage that can be transplanted to an articular cartilage defect site.

Solution to Problem

The present invention includes the following to achieve the above-mentioned object.

[1] A plate-shaped cartilage comprising a plurality of pluripotent stem cell-derived cartilaginous particles integrated with one another.

[2] The plate-shaped cartilage according to the above [1], wherein the plate-shaped cartilage is for transplantation to a cartilage injury site.

[3] A method for producing the plate-shaped cartilage according to the above [1] or [2], the method comprising step 1: producing pluripotent stem cell-derived cartilaginous particles, and step 2: culturing the cartilaginous particles under culture conditions that allow adjacent cartilaginous particles to be in contact with one another, wherein the number of the cartilaginous particles is that required to form the plate-shaped cartilage.

[4] The method according to the above [3], wherein, in step 2, the required number of the cartilaginous particles is contained in a liquid-permeable vessel or in a frame placed in culture medium.

[5] The method according to the above [4], wherein the vessel can contain a single layer of the required number of the cartilaginous particles.

[6] The method according to any one of the above [3] to [5], wherein the cartilaginous particles are in process of growth.

[7] The method according to any one of the above [3] to [6], wherein the culturing in step 2 is performed in culture medium under flow conditions.

[8] The method according to any one of the above [3] to [7], wherein the culturing in step 2 is performed in culture medium comprising a fibroblast growth factor (FGF) receptor agonist.

[9] The method according to the above [8], wherein the FGF receptor agonist is FGF18.

[10] A pharmaceutical composition for injured cartilage repair, comprising the plate-shaped cartilage according to the above [1] or [2].

[11] A cartilage repair method comprising the step of transplanting the plate-shaped cartilage according to the above [1] or [2] to a cartilage defect site.

[12] [9] The plate-shaped cartilage according to the above [1] or [2], which is for cartilage repair.

[13] Use of the plate-shaped cartilage according to the above [1] or [2] for production of a pharmaceutical composition for injured cartilage repair.

Advantageous Effects of Invention

The present invention provides a pluripotent stem cell-derived plate-shaped cartilage. The plate-shaped cartilage of the present invention can be transplanted after formed and optionally trimmed to fit the size of an articular cartilage defect site. Therefore, the plate-shaped cartilage of the present invention is useful as a pharmaceutical composition for regenerative therapy for joint injury. The present invention is characterized by integration of cartilaginous particles before transplantation, which reduces the possibility of cartilaginous particle falling out after transplantation, which is a problem of conventional techniques. According to the present invention, a pluripotent stem cell-derived cartilage tissue that fits the size of a defect site can be transplanted, and transplantation of such a tissue treats a wider variety of defects and degenerations in articular cartilage.

BRIEF DESCRIPTION OF DRAWINGS

FIG. 13A shows a cartilage formed in the polycarbonate transwell. FIG. 13B shows a cartilage formed in the polyester transwell.

DESCRIPTION OF EMBODIMENTS

Plate-Shaped Cartilage

Figure 1:
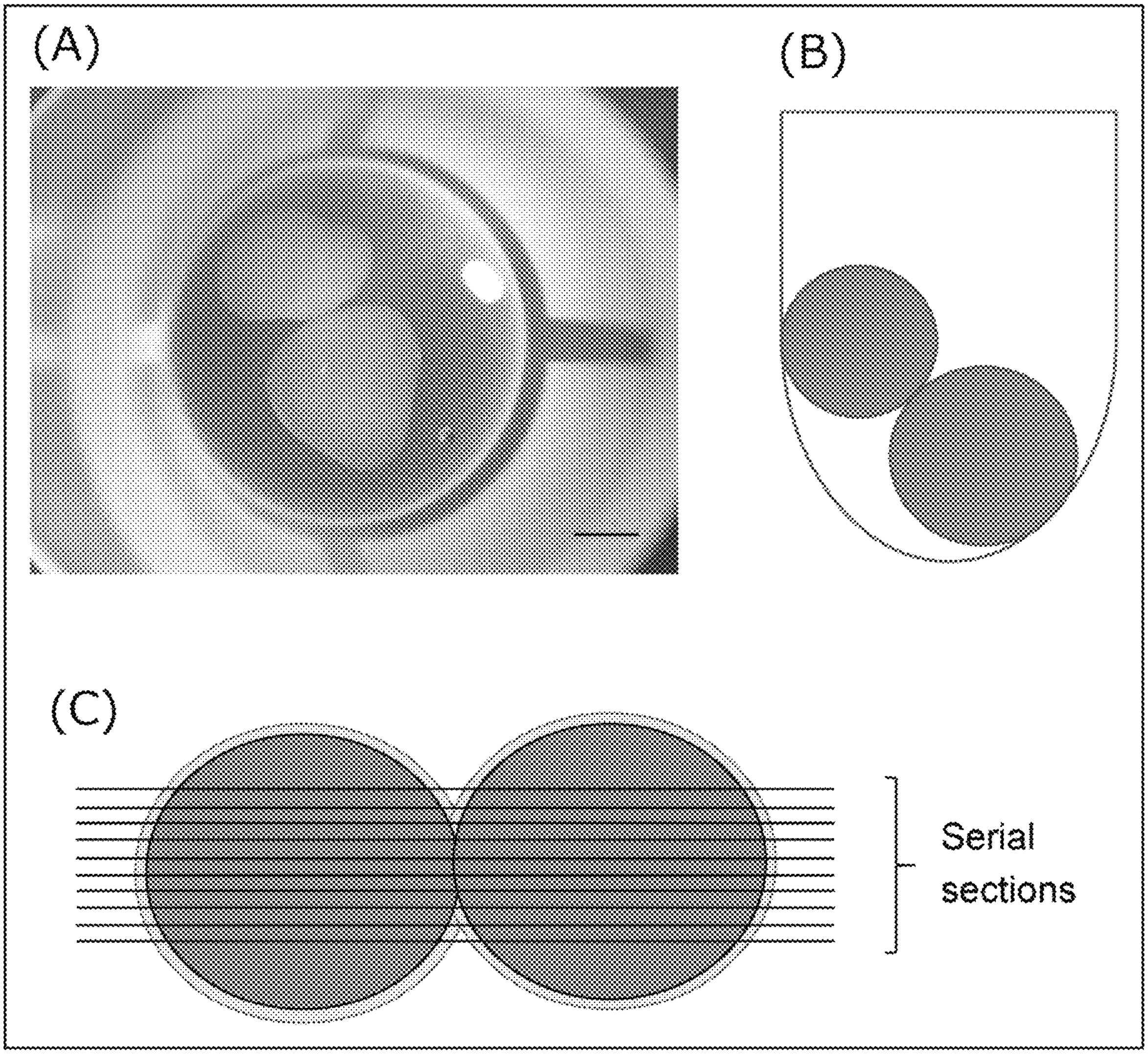
FIG. 1A shows an image of a well of a round-bottom 96-well plate that contains a pair of human iPS cell-derived cartilaginous particles.
FIG. 1B is a schematic of the well of FIG. 1A.
FIG. 1C is a schematic of serial sections of integrated human iPS cell-derived cartilaginous particles.

The present invention provides a pluripotent stem cell-derived plate-shaped cartilage. The plate-shaped cartilage of the present invention is a plate-shaped cartilage (plate-shaped cartilaginous tissue) comprising a plurality of pluripotent stem cell-derived cartilaginous particles integrated with one another. The plate-shaped cartilage of the present invention may be a plate-shaped cartilage comprising a multiple layer of a plurality of pluripotent stem cell-derived cartilaginous particles integrated with one another, or comprising a single layer of a plurality of pluripotent stem cell-derived cartilaginous particles integrated with one another.

The plate-shaped cartilage of the present invention may have the same thickness as that of a cartilage present in the living body (native cartilage). For example, the thickness of the plate-shaped cartilage may be 5 mm or less, 4 mm or less, 3 mm or less, or 2 mm or less. The thickness of the plate-shaped cartilage may be about 1.5 to 4.5 mm, about 2 to 4 mm, or about 2.5 to 3.5 mm. The thickness of the plate-shaped cartilage can be defined as the mean of the thicknesses of more than one sites in the plate-shaped cartilage, and the plate-shaped cartilage may have a portion thicker than the specified thickness.

The plate-shaped cartilage of the present invention is suitable for transplantation to a cartilage injury site. The plate-shaped cartilage of the present invention can be transplanted after formed and optionally trimmed to fit the shape and size of a cartilage defect site at the cartilage injury site; therefore it is very useful. The plate-shaped cartilage of the present invention has the same thickness as that of an articular cartilage and therefore is suitable particularly for transplantation to an articular cartilage injury site. The plate-shaped cartilage of the present invention can be remodeled in the living body after transplantation. For this reason, the plate-shaped cartilage of the present invention is not required to have the exact same shape, size, and thickness as those of the transplantation site.

Pluripotent stem cells that can be used for the production of the cartilaginous particles are not particularly limited as long as they are stem cells having both pluripotency, by which the cells are capable of differentiating into any types of cells in the living body, and proliferation potency. Examples of the pluripotent stem cells include embryonic stem (ES) cells, embryonic stem cells from clone embryos obtained by nuclear transplantation (nuclear transfer ES (ntES) cells), spermatogonial stem cells (germline stem (GS) cells), embryonic germ cells (EG cells), induced pluripotent stem (iPS) cells, and pluripotent cells (Muse cells) derived from cultured fibroblasts or myeloid stem cells. Preferred pluripotent stem cells are ES cells, ntES cells, and iPS cells.

(A) Embryonic Stem Cells

ES cells are stem cells having pluripotency and proliferation potency via self-replication and are established from the inner cell mass of early embryos (e.g., blastocysts) of mammals such as humans and mice.

ES cells are stem cells derived from the inner cell mass of a blastocyst, an embryo that has developed beyond the morula and eight-cell stages from a fertilized egg. ES cells have so-called pluripotency, by which they are capable of differentiating into any types of cells composing an adult body, and proliferation potency via self-replication. ES cells were discovered in mice in 1981 (M. J. Evans and M. H. Kaufman (1981), Nature 292:154-156). Thereafter, ES cell lines were established in primates including humans, monkeys, etc. (J. A. Thomson et al. (1998), Science 282:1145-1147; J. A. Thomson et al. (1995), Proc. Natl. Acad. Sci. USA, 92:7844-7848; J. A. Thomson et al. (1996), Biol. Reprod., 55:254-259; J. A. Thomson and V. S. Marshall (1998), Curr. Top. Dev. Biol., 38:133-165).

ES cells can be established by harvesting the inner cell mass from blastocysts developed from fertilized eggs of animals and then culturing the inner cell mass on fibroblasts as feeders. Cell maintenance by subculture can be performed using a medium supplemented with substances such as leukemia inhibitory factor (LIF) and basic fibroblast growth factor (bFGF). Methods for establishment and maintenance of human and monkey ES cells are described in, for example, USP 5, 843, 780; Thomson J A, et al. (1995), Proc Natl. Acad. Sci. USA. 92:7844-7848; Thomson J A, et al. (1998), Science. 282:1145-1147; H. Suemori et al. (2006), Biochem. Biophys. Res. Commun., 345:926-932; M. Ueno et al. (2006), Proc. Natl. Acad. Sci. USA, 103:9554-9559; H. Suemori et al. (2001), Dev. Dyn., 222:273-279; H. Kawasaki et al. (2002), Proc. Natl. Acad. Sci. USA, 99:1580-1585; Klimanskaya I, et al. (2006), Nature. 444:481-485; etc.

Human ES cells can be maintained under a humid atmosphere of 2% $CO_2$/98% air at 37° C. in a culture medium for preparation of ES cells, for example, a DMEM/F-12 medium supplemented with 0.1 mM 2-mercaptoethanol, 0.1 mM non-essential amino acids, 2 mM L-glutamic acid, 20% KnockOut Serum Replacement (KSR, Invitrogen), and 4 ng/mL bFGF (O. Fumitaka et al. (2008), Nat. Biotechnol., 26:215-224). ES cells need to be subcultured every 3 to 4 days. The subculture can be performed using, for example, 0.25% trypsin and 0.1 mg/ml collagenase IV in PBS containing 1 mM $CaCl_2$ and 20% KSR.

ES cells can be generally selected based on the expression of gene markers as an indicator, such as alkaline phosphatase, Oct-3/4, and Nanog. The markers can be detected by real-time PCR. In particular, for selection of human ES cells, the expression of gene markers such as OCT-3/4, NANOG, and ECAD can be used as an indicator (E. Kroon et al. (2008), Nat. Biotechnol., 26:443-452).

Human ES cell lines, for example, WA01 (H1) and WA09 (H9) are available from WiCell Research Institute, Inc., and KhES-1, KhES-2, and KhES-3 are available from the Institute for Frontier Medical Sciences, Kyoto University (Kyoto, Japan).

(B) Spermatogonial Stem Cells

Spermatogonial stem cells are testis-derived pluripotent stem cells, serving as an origin for spermatogenesis. As with ES cells, spermatogonial stem cells can also be induced to differentiate into cells of various lineages. For example, the transplantation of spermatogonial stem cells into mouse blastocysts can generate chimeric mice (M. Kanatsu-Shinohara et al. (2003) Biol. Reprod., 69:612-616; K. Shinohara et al. (2004), Cell, 119:1001-1012). In addition, spermatogonial stem cells are self-replicable in a medium containing glial cell line-derived neurotrophic factor (GDNF), and spermatogonial stem cells can be obtained by repeated subculture under culture conditions similar to those for ES cell establishment (Masanori Takebayashi et al., (2008), Experimental Medicine, Vol. 26, No. 5 (Extra Number), pp. 41-46, YODOSHA (Tokyo, Japan)).

(C) Embryonic Germ Cells

Embryonic germ cells are cells established from primordial germ cells at the embryonic period and have pluripotency like ES cells. Embryonic germ cells can be established by culturing primordial germ cells in the presence of substances such as LIF, bFGF, and stem cell factor (Y. Matsui et al. (1992), Cell, 70:841-847; J. L. Resnick et al. (1992), Nature, 359:550-551).

(D) Induced Pluripotent Stem Cells

Induced pluripotent stem (iPS) cells can be generated by introducing specific reprogramming factors in the form of DNA or protein into somatic cells. iPS cells are somatic cell-derived artificial stem cells having almost the same properties as those of ES cells, such as pluripotency and proliferation potency via self-replication (K. Takahashi and S. Yamanaka (2006) Cell, 126:663-676; K. Takahashi et al. (2007), Cell, 131:861-872; J. Yu et al. (2007), Science, 318:1917-1920; Nakagawa, M. et al., Nat. Biotechnol. 26:101-106 (2008); WO 2007/069666). The reprogramming factor may be a gene specifically expressed in ES cells, a gene product or non-coding RNA thereof, a gene playing an important role in the maintenance of the undifferentiated state of ES cells, a gene product or non-coding RNA thereof, or a low-molecular-weight compound. Examples of the gene serving as the reprogramming factor include, for example, Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, β-catenin, Lin28b, Sall1, Sall4, Esrrb, Nr5a2, Tbx3 and Glis1. One of these reprogramming factors may be used alone, and also two or more of them may be used in combination. Examples of the combination of such reprogramming factors include those described in WO 2007/069666, WO 2008/118820, WO 2009/007852, WO 2009/032194, WO 2009/058413, WO 2009/057831, WO 2009/075119, WO 2009/079007, WO 2009/091659, WO 2009/101084, WO 2009/101407, WO 2009/102983, WO 2009/114949, WO 2009/117439, WO 2009/126250, WO 2009/126251, WO 2009/126655, WO 2009/157593, WO 2010/009015, WO 2010/033906, WO 2010/033920, WO 2010/042800, WO 2010/050626, WO 2010/056831, WO 2010/068955, WO 2010/098419, WO 2010/102267, WO 2010/111409, WO 2010/111422, WO 2010/115050, WO 2010/124290, WO 2010/147395, WO 2010/147612, Huangfu D, et al. (2008), Nat. Biotechnol., 26:795-797, Shi Y, et al. (2008), Cell Stem Cell, 2:525-528, Eminli S, et al. (2008), Stem Cells. 26:2467-2474, Huangfu D, et al. (2008), Nat Biotechnol. 26:1269-1275, Shi Y, et al. (2008), Cell Stem Cell, 3, 568-574, Zhao Y, et al. (2008), Cell Stem Cell, 3:475-479, Marson A, (2008), Cell Stem Cell, 3, 132-135, Feng B, et al. (2009), Nat Cell Biol. 11:197-203, R. L. Judson et al., (2009), Nat. Biotech., 27:459-461, Lyssiotis C A, et al. (2009), Proc Natl Acad Sci USA. 106:8912-8917, Kim J B, et al. (2009), Nature. 461:649-643, Ichida J K, et al. (2009), Cell Stem Cell. 5:491-503, Heng J C, et al. (2010), Cell Stem Cell. 6:167-74, Han J, et al. (2010), Nature. 463:1096-100, Mali P, et al. (2010), Stem Cells. 28:713-720, and Maekawa M, et al. (2011), Nature. 474: 225-9.

Other examples of the reprogramming factor include factors used for enhancing the establishment efficiency, such as histone deacetylase (HDAC) inhibitors [e.g., low-molecular-weight inhibitors such as valproic acid (VPA), trichostatin A, sodium butyrate, MC 1293, and M344, and nucleic acid-based expression inhibitors such as siRNA and shRNA against HDAC (e.g., HDAC1 siRNA Smartpool (Millipore), HuSH 29-mer shRNA Constructs against HDAC1 (OriGene), etc.], MEK inhibitors (e.g., PD184352, PD98059, U0126, SL327 and PD0325901), glycogen synthase kinase-3 inhibitors (e.g., Bio and CHIR99021), DNA methyltransferase inhibitors (e.g., 5-azacytidine), histone methyltransferase inhibitors (e.g., low-molecular-weight inhibitors such as BIX-01294, and nucleic acid-based expression inhibitors such as siRNA and shRNA against Suv39 h1, Suv39 h2, SetDB1, or G9a), L-channel calcium agonists (e.g., Bayk8644), butyric acid, TGFβ inhibitors, or ALK5 inhibitors (e.g., LY364947, SB431542, 616453, and A-83-01), p53 inhibitors (e.g., siRNA and shRNA against p53), ARID3A inhibitors (e.g., siRNA and shRNA against ARID3A), miRNAs such as miR-291-3p, miR-294, miR-295, and mir-302, Wnt signaling (e.g., soluble Wnt3a), neuropeptide Y, prostaglandins (e.g., prostaglandin E2 and prostaglandin J2), hTERT, SV40LT, UTF1, IRX6, GLIS1, PITX2, DMRTB1, etc. These factors used for enhancing the establishment efficiency are not distinguished from the reprogramming factors in the present invention.

The reprogramming factors may be introduced in the form of protein into somatic cells by a technique such as lipofection, fusion with a cell membrane-permeable peptide (e.g., HIV TAT and polyarginine), and microinjection.

Alternatively, the reprogramming factors may be introduced in the form of DNA into somatic cells by a technique such as a technique using a vector (such as a viral vector, a plasmid vector, and an artificial chromosome vector), lipofection, a technique using a liposome, and microinjection. Examples of the viral vector include retroviral vectors, lentiviral vectors (both described in Cell, 126, pp. 663-676, 2006; Cell, 131, pp. 861-872, 2007; Science, 318, pp. 1917-1920, 2007), adenoviral vectors (Science, 322, 945-949, 2008), adeno-associated viral vectors, and Sendai virus vectors (WO 2010/008054). Examples of the artificial chromosome vector include human artificial chromosome (HAC) vectors, yeast artificial chromosome (YAC) vectors, and bacterial artificial chromosome (BAC, PAC) vectors. Examples of the plasmid vector include plasmids for mammalian cells (Science, 322:949-953, 2008). Such a vector can contain regulatory sequences such as a promoter, an enhancer, a ribosome binding sequence, a terminator, and a polyadenylation site, so that a nuclear reprogramming factor can be expressed. The vector may further contain, if necessary, a selection marker sequence such as a drug resistance gene (e.g., a kanamycin resistance gene, an ampicillin resistance gene, and a puromycin resistance gene), a thymidine kinase gene, and a diphtheria toxin gene; a reporter gene sequence such as a green fluorescent protein (GFP), β-glucuronidase (GUS), and FLAG; and/or other sequences. In order to remove a gene encoding a reprogramming factor or remove a promoter together with a gene encoding a reprogramming factor binding thereto after introduction of the vector into somatic cells, LoxP sequences may be inserted upstream and downstream of the region to be removed.

Alternatively, the reprogramming factors may be introduced in the form of RNA into somatic cells by a technique such as lipofection and microinjection. In order to prevent decomposition, RNAs containing 5-methylcytidine and pseudouridine (TriLink BioTechnologies) may be used (Warren L (2010), Cell Stem Cell. 7:618-630).

The culture medium for iPS cell generation is, for example, DMEM, DMEM/F12 or DME medium containing 10 to 15% FBS (these media may further contain LIF, penicillin/streptomycin, puromycin, L-glutamine, non-essential amino acids, β-mercaptoethanol, etc. as needed), or a commercially available medium such as a medium for mouse ES cell culture (e.g., TX-WES medium (Thromb-X)), a medium for primate ES cell culture (e.g., a medium for primate ES/iPS cells (ReproCELL)), and a serum-free medium for maintenance of pluripotent stem cells (e.g., mTeSR (STEMCELL Technologies), Essential 8 (Life Technologies), and StemFit AK03 (AJINOMOTO)).

An exemplary culture method is as follows. Somatic cells are brought into contact with reprogramming factors in a DMEM or DMEM/F12 medium containing 10% FBS at 37° C. in an atmosphere of 5% $CO_2$ and then cultured for about 4 to 7 days. The cells are then reseeded on feeder cells (e.g., mitomycin C-treated STO cells, SNL cells, etc.). At about 10 days after contact between the somatic cells and the reprogramming factors, the medium is changed to a bFGF-containing medium for primate ES cell culture, and cell culture is further continued. At about 30 to 45 days or more after the contact, iPS cell-like colonies appear.

Alternatively, the cells are cultured on feeder cells (e.g., mitomycin C-treated STO cells, SNL cells, etc.) in a 10% FBS-containing DMEM medium (this medium may further contain LIF, penicillin/streptomycin, puromycin, L-glutamine, non-essential amino acids, β-mercaptoethanol, etc. as needed) at 37° C. in an atmosphere of 5% $CO_2$. At about 25 to 30 days or more after the start of culture, ES-like colonies appear. Preferably, instead of feeder cells, the somatic cells to be reprogrammed are used as feeder cells (Takahashi K, et al. (2009), PLOS One. 4: e8067, or WO 2010/137746), or alternatively, an extracellular matrix (e.g., laminin-5 (WO 2009/123349) or Matrigel (BD)) is used.

Alternatively, the cells may be cultured in a serum-free medium (Sun N, et al. (2009), Proc Natl Acad Sci USA. 106:15720-15725). For enhancing the establishment efficiency of iPS cells, low oxygen conditions (oxygen concentration of 0.1 to 15%) may be employed (Yoshida Y, et al. (2009), Cell Stem Cell. 5:237-241, or WO 2010/013845).

During the above culture, medium change to a fresh medium is performed once daily after day 2 of culture. The number of somatic cells to undergo nuclear reprogramming is not limited and is, for example, within the range of about $5\times10^3$ to $5\times10^6$ cells per culture dish (100 $cm^2$).

iPS cells can be selected based on the shape of the colonies. When a drug resistance gene to be expressed along with the gene to be expressed in reprogrammed somatic cells (e.g., Oct3/4, Nanog) has been introduced as a marker gene, established iPS cells can be selected by culturing the cells in a medium containing the relevant drug (selective medium). When a fluorescent protein gene is used as a marker gene, iPS cells of interest can be selected by observation under a fluorescence microscope. When a luminescent enzyme gene is used as a marker gene, iPS cells of interest can be selected by adding a luminescent substrate. When a chromogenic enzyme gene is used as a marker gene, iPS cells of interest can be selected by adding a chromogenic substrate.

The term "somatic cells" as used herein refers to any types of animal cells (preferably mammalian cells including human cells) other than germ cells or totipotent cells such as ova, oocytes, and ES cells. Somatic cells include, but are not limited to, somatic cells of fetuses, somatic cells of neonates, and mature healthy or pathological somatic cells, as well as primary cultured cells, passaged cells, and established cell lines. Specific examples of the somatic cells include (1) tissue stem cells (somatic stem cells), such as neural stem cells, hematopoietic stem cells, mesenchymal stem cells, and dental pulp stem cells,
(2) tissue progenitor cells, and
(3) differentiated cells, such as lymphocytes, epithelial cells, endothelial cells, muscle cells, fibroblasts (skin cells etc.), hair cells, hepatocytes, gastric mucosal cells, enterocytes, splenocytes, pancreatic cells (pancreatic exocrine cells etc.), brain cells, lung cells, renal cells, and adipocytes.

When iPS cells are used to generate cells to be transplanted, the iPS cells are preferably produced from somatic cells having the same or substantially the same HLA alleles as those of the recipient to prevent rejection. The term "substantially the same" herein means that the HLA alleles match to the extent that immune response against the transplanted cells can be suppressed by an immunosuppressant. The somatic cells have, for example, three matched HLA alleles including HLA-A, HLA-B and HLA-DR or four matched HLA alleles further including HLA-C.

(E) ES Cells Derived from Clone Embryos Generated by Nuclear Transplantation ntES (nuclear transfer ES) cells are ES cells derived from clone embryos generated by nuclear transplantation techniques. ntES cells have almost the same properties as those of fertilized egg-derived ES cells (T. Wakayama et al. (2001), Science, 292:740-743; S. Wakayama et al. (2005), Biol. Reprod., 72:932-936; J. Byrne et al. (2007), Nature, 450:497-502). Specifically, ntES cells are ES cells established from the blastocyst inner cell mass of a clone embryo obtained via replacement of the nucleus of an unfertilized egg with the nucleus of a somatic cell. For preparation of ntES cells, nuclear transplantation techniques (J. B. Cibelli et al. (1998), Nature Biotechnol., 16:642-646) and the above ES cell preparation techniques are used in combination (Kiyoka Wakayama et al., (2008), Experimental Medicine, Vol. 26, No. 5 (Extra Number), pp. 47-52). In nuclear transplantation, the nucleus of a somatic cell is injected into a mammalian enucleated unfertilized egg, and then the resulting cell is cultured for several hours so as to undergo reprogramming.

(F) Multilineage-Differentiating Stress Enduring Cells (Muse Cells)

Muse cells are pluripotent stem cells produced by the method described in WO 2011/007900. Specifically, Muse cells are pluripotent cells produced by subjecting fibroblasts or bone marrow stromal cells to trypsin treatment for a long period of time, preferably 8 or 16 hours, and then culturing the cells in suspension. Muse cells are SSEA-3 and CD105 positive.

Method for Producing a Plate-Shaped Cartilage

The present invention provides a method for producing the plate-shaped cartilage described above. The production method of the present invention comprises the following steps:

step 1: producing pluripotent stem cell-derived cartilaginous particles, and step 2: culturing the cartilaginous particles under culture conditions that allow adjacent cartilaginous particles to be in contact with one another, wherein the number of the cartilaginous particles is that required to form the plate-shaped cartilage.

Step 1 is a step of producing pluripotent stem cell-derived cartilaginous particles. The method for inducing pluripotent stem cells to differentiate into cartilaginous particles is known, and an appropriate method may be selected from the methods described in, for example, Patent Literature 1, Non Patent Literature 1, Non Patent Literature 2, etc. Apreferable method is specifically described below, but the method of the present invention for producing pluripotent stem cell-derived cartilaginous particles is not limited thereto.

The method used in step 1 of the production method of the present invention may comprise the following steps:

(i) culturing pluripotent stem cells under adherent conditions in a culture medium containing a hydroxymethylglutaryl-CoA (HMG-COA) reductase inhibitor and one or more substances selected from the group consisting of bone morphogenetic protein (BMP) 2, transforming growth factor (TGF) β, and growth differentiator (GDF) 5, and (ii) culturing the cells obtained in step (i) under suspension conditions in a culture medium containing an HMG-COA reductase inhibitor and one or more substances selected from the group consisting of BMP2, TGFβ, and GDF5.

The pluripotent stem cells to be used in step (i) are preferably in the form of a cell cluster formed in three-dimensional suspension culture under the conditions that allow the cells to retain their undifferentiated state. The three-dimensional suspension culture in the present invention is a culture method in which cells are cultured under non-adherent conditions with stirring or agitation in culture medium.

In the cell clusters of more than 300 μm in diameter, cytokines etc. secreted from cells in the clusters may induce cell differentiation, and necrosis may occur inside the cell clusters. For these reasons, the diameter of the cell clusters needs to be adjusted to not more than 300 μm. The adjustment of the diameter of the cell clusters can be achieved by, for example, adjusting cell density and stirring speed as appropriate and/or selecting cell clusters of an appropriate size.

The culture medium used in step (i) can be prepared by adding an HMG-CoA reductase inhibitor and one or more substances selected from the group consisting of BMP2, TGFβ, and GDF5 to a basal medium for animal cell culture. A preferable culture medium used in step (i) is a basal medium supplemented with BMP2, TGFβ, GDF5, and an HMG-COA reductase inhibitor. Examples of the basal medium include IMDM, Medium 199, Eagle's minimum essential medium (EMEM), αMEM, Dulbecco's modified Eagle's medium (DMEM), Ham's F12 medium, RPMI 1640 medium, Fischer's medium, and a mixed medium thereof. As needed, the basal medium may contain an additional ingredient such as serum (e.g., FBS), albumin, transferrin, KnockOut Serum Replacement (KSR) (serum substitute for FBS in ES cell culture) (Invitrogen), N2 supplement (Invitrogen), B27 supplement (Invitrogen), fatty acids, insulin, sodium selenite, ethanolamine, collagen progenitors, trace elements, 2-mercaptoethanol, 3'-thiolglycerol, lipids, amino acids, L-glutamine, GlutaMAX (Invitrogen), non-essential amino acids (NEAAs), sodium pyruvate, vitamins, growth factors, low-molecular-weight compounds, antibiotics, antioxidants, pyruvic acid, buffering agents, and inorganic salts. In one embodiment of step (i), the basal medium is DMEM containing insulin, transferrin, sodium selenite, ethanolamine, ascorbic acid, non-essential amino acids, sodium pyruvate, antibiotics, and serum.

The BMP2 in step (i) includes human BMP2, non-human BMP2, and functionally modified derivatives thereof. The BMP2 may be, for example, a commercially available product from Osteopharma etc. The concentration of BMP2 used in this step is 0.1 to 1000 ng/mL, preferably 1 to 100 ng/mL, more preferably 5 to 50 ng/mL, in particular 10 ng/ml. BMP2 may be replaced with BMP4 in the present invention.

The TGFβ in step (i) includes human TGFβ, non-human TGEβ, and functionally modified derivatives thereof. The TGEβ may be, for example, a commercially available product from PeproTech etc. The concentration of TGEβ used in this step is 0.1 to 1000 ng/ml, preferably 1 to 100 ng/ml, more preferably 5 to 50 ng/ml, in particular 10 ng/mL.

The GDF5 in step (i) includes human GDF5, non-human GDF5, and functionally modified derivatives thereof. The GDF5 may be, for example, a commercially available product from PeproTech etc. The concentration of GDF5 used in this step is 0.1 to 1000 ng/ml, preferably 1 to 100 ng/ml, more preferably 5 to 50 ng/ml, in particular 10 ng/mL.

Examples of the HMG-COA reductase inhibitor used in step (i) include, but are not limited to, mevastatin (compactin) (see U.S. Pat. No. 3,983,140), pravastatin (see JP-A 57-2240 (U.S. Pat. No. 4,346,227)), lovastatin (see JP-A 57-163374 (U.S. Pat. No. 4,231,938)), simvastatin (see JP-A 56-122375 (U.S. Pat. No. 4,444,784)), fluvastatin (see JP-W 60-500015 (U.S. Pat. No. 4,739,073)), atorvastatin (see JP-A 3-58967 (U.S. Pat. No. 5,273,995)), rosuvastatin (see JP-A 5-178841 (U.S. Pat. No. 5,260,440)), and pitavastatin (see JP-A 1-279866 (U.S. Pat. Nos. 5,854,259 and 5,856,336)). The HMG-COA reductase inhibitor used in the present invention is preferably selected from the group consisting of mevastatin, atorvastatin, pravastatin, rosuvastatin, fluvastatin, and lovastatin.

When rosuvastatin is used as the HMG-COA reductase inhibitor in step (i), the concentration is 0.01 μM to 100 μM, preferably 0.1 μM to 10 μM, more preferably 0.5 μM to 5 μM, in particular 1 μM.

In step (i), the basal medium may be further supplemented with bFGF. The bFGF includes human bFGF, non-human bFGF, and functionally modified derivatives thereof. The bFGF may be, for example, a commercially available product from WAKO etc. The concentration of bFGF used in this step is 0.1 to 1000 ng/ml, preferably 1 to 100 ng/ml, more preferably 5 to 50 ng/ml, in particular 10 ng/ml.

In step (i), the basal medium may be further supplemented with a pterosin derivative. The pterosin derivative is, for example, the same as described in 14/315,809, preferably pterosin B. The concentration of pterosin B used in this step is 10 μM to 1000 μM, preferably 100 μM to 1000 μM.

As used herein, "culturing under adherent conditions" refers to culturing cells in an adherent state on the surface of a culture vessel. The culture vessel used is not particularly limited as long as it is usable for adherent culture of cultured cells. Examples of the culture vessel include a flask, a tissue culture flask, a dish, a Petri dish, a tissue culture dish, a multidish, a microplate, a microwell plate, a multiplate, a multiwell plate, a chamber slide, a culture slide, and a Petri dish. The culture vessel may have a surface subjected to treatment to facilitate cell attachment or a surface not subjected to such treatment (a non-coated surface). The culture vessel having a surface subjected to treatment to facilitate cell attachment may be a commercially available product, for example, a tissue culture dish available from IWAKI. In another embodiment, culturing under adherent conditions is performed using a culture vessel coated with an extracellular matrix. The coating treatment can be achieved by adding a solution containing an extracellular matrix to a culture vessel, followed by removing the solution at an appropriate timing.

The extracellular matrix used for coating may be naturally occurring or artificial (recombinant). Examples of the extracellular matrix include polylysine, polyornithine, collagens, proteoglycans, fibronectins, hyaluronic acid, tenascins, entactins, elastins, fibrillins, laminins, and fragments of these substances. These extracellular matrices may be used in combination as needed.

The culture temperature in step (i) is not particularly limited and is, for example, about 30 to 40° C., preferably about 37° C. The culture is performed under an atmosphere of air with $CO_2$. The $CO_2$ concentration is about 2 to 5%, preferably about 5%. The culture period in step (i) is not particularly limited as long as it is longer than a period of time required for the seeded cell clusters to adhere to the culture vessel and form nodules. The culture period in step (i) may be 7 days or more, 14 days or more, 21 days or more, or 28 days or more. In addition, the culture period in step (i) may be 35 days or less, 28 days or less, 21 days or less, or 14 days or less. Preferably, the culture period in step (i) is 14 days.

In step (i), the nodular cells may be present in a suspended state after spontaneous detachment from the surface of the culture vessel during the culture period. In some cases, the cells may remain adherent on the surface of the culture vessel until the end of the culture period. The spontaneously detached and suspended nodules (cell clusters) are directly subjected to suspension culture in step (ii). The nodules (cell clusters) adherent on the surface of the culture vessel are first detached from the surface of the culture vessel and then subjected to suspension culture in step (ii). The detachment of the nodules (cell clusters) from the surface of the culture vessel is preferably performed by mechanical means (e.g., pipetting or using a scraper etc.), not using a detachment solution with protease activity and/or collagenase activity (e.g., solutions containing trypsin and collagenase, such as Accutase™ and Accumax™ (Innovative Cell Technologies, Inc.)).

Step (ii) is a step of culturing the cells obtained in step (i) under suspension conditions. As used herein, "culturing under suspension conditions" refers to culturing cells in a state in which the cells are not adherent on the surface of a culture vessel. This can be performed in various ways without particular limitation. Preferably, "culturing under suspension conditions" is performed using a culture vessel (e.g., a Petri dish) without artificial treatment for enhancing cell attachment to the vessel (e.g., coating treatment using an extracellular matrix etc.) or a culture vessel with artificial treatment for preventing cell attachment to the vessel (e.g., coating treatment using polyhydroxyethyl methacrylate (poly-HEMA)).

The culture medium used in step (ii) may be the same as described above in step (i).

The culture temperature in step (ii) is not particularly limited and is, for example, about 30 to 40° C., preferably about 37° C. The culture is performed under an atmosphere of air with $CO_2$. The $CO_2$ concentration is about 2 to 5%, preferably about 5%. The culture period is not particularly limited, and culture can be continued until desired cartilaginous particles are obtained. The culture period in step (ii) may be 7 days or more, 14 days or more, 21 days or more, 28 days or more, 35 days or more, 42 days or more, 49 days or more, 56 days or more, 63 days or more, or 70 days or more. The culture period in step (ii) may be 140 days or less, 133 days or less, 126 days or less, 119 days or less, 112 days or less, 105 days or less, 98 days or less, 91 days or less, 84 days or less, 77 days or less, 70 days or less, 63 days or less, 56 days or less, 49 days or less, 42 days or less, 35 days or less, 28 days or less, 21 days or less, or 14 days or less. The production of cartilaginous particles can be confirmed by sampling some particles from the culture and staining them with safranin 0.

Step 2 is a step of culturing the cartilaginous particles under culture conditions that allow adjacent cartilaginous particles to be in contact with one another, wherein the number of the cartilaginous particles is that required to form the plate-shaped cartilage. The cartilaginous particles used in step 2 are the cartilaginous particles produced in step 1. The present inventor and others previously confirmed that the cartilaginous particle size changes along with the number of days after the start of the differentiation (the day when the medium is changed to a chondrogenic differentiation medium) in step 1. More specifically, the present inventor and others previously confirmed that the cartilaginous particles grow to a size (diameter) of about 1 mm at 4 weeks and about 2 to 3 mm at 12 weeks after the start of the differentiation, and thereafter stop growing at a size of about 3 to 4 mm even when culture is continued. The cartilaginous particles used in step 2 may be cartilaginous particles at less than 4 weeks (28 days), cartilaginous particles at 4 weeks (28 days) to 6 weeks (42 days), cartilaginous particles at 6 weeks (42 days) to 8 weeks (56 days), cartilaginous particles at 8 weeks (56 days) to 10 weeks (70 days), cartilaginous particles at 10 weeks (70 days) to 12 weeks (84 days), cartilaginous particles at 12 weeks (84 days) to 14 weeks (98 days), or cartilaginous particles at more than 14 weeks (98 days) after the start of the differentiation in step 1. Preferred are cartilaginous particles in process of growth. The cartilaginous particles in process of growth are preferably cartilaginous particles at 6 weeks (42 days) or less, 5 weeks (35 days) or less, or 4 weeks (28 days) or less after the start of the differentiation, and more preferably cartilaginous particles at about 4 weeks (25 to 32 days) after the start of the differentiation.

The required number of the cartilaginous particles can be determined as appropriate for the size of the desired plate-shaped cartilage. In the case where the cartilaginous particles used in step 2 are cartilaginous particles in process of growth, the required number of the cartilaginous particles is preferably adjusted in consideration of cartilaginous particle growth during the culture period in step 2.

In step 2, a frame that can be placed in culture medium can preferably be used for culturing the cartilaginous particles under culture conditions that allow adjacent cartilaginous particles to be in contact with one another. For example, medium is added to a culture dish, and a suitable frame is then disposed therein. More specifically, the frame may be a smaller-size culture dish, a transwell for chemotaxis testing, or the like. The cartilaginous particles produced in step 1 are placed in the frame. Preferably, the cartilaginous particles are placed in the frame such that adjacent cartilaginous particles are in contact with one another and such that the cartilaginous particles form a single layer.

In step 2, a liquid-permeable vessel can preferably be used for culturing the cartilaginous particles under culture conditions that allow adjacent cartilaginous particles to be in contact with one another. The liquid-permeable vessel may be a mesh bag for biopsy sample storage or the like. The size of the mesh bag is determined according to the desired size of the plate-shaped cartilage. The cartilaginous particles produced in step 1 are placed in the mesh bag, and culture medium is added thereto. The required number of the cartilaginous particles placed in the mesh bag is not particularly limited. The required number may be a number allowing the formation of a single closest-packed layer in the mesh bag, or a number corresponding to about 90%, about 80%, about 70%, about 60%, about 50%, about 40%, or about 30% of the number allowing the formation of a single closest-packed layer in the mesh bag. In the case where the cartilaginous particles used in step 2 are cartilaginous particles in process of growth, the required number of the cartilaginous particles is preferably adjusted in consideration of cartilaginous particle growth during the culture period in step 2.

In the case where the cartilaginous particles are cultured in the liquid-permeable vessel in step 2, they are preferably cultured in culture medium under flow conditions. Culturing in culture medium under flow conditions can be performed using a bioreactor, for example. More specifically, a liquid-permeable vessel containing the cartilaginous particles is placed in culture medium in a bioreactor, and the culture medium is perfused. The bioreactor used is not particularly limited, and a preferable example is a bioreactor with a magnetic stirrer manufactured by ABLE Corporation. The present inventor and others previously confirmed that plate-shaped cartilage formation is promoted in culture medium under flow conditions.

The culture medium used in step 2 can be the same as the culture medium used in step 1 (i) except for the absence of the HMG-COA reductase inhibitor.

The culture medium used in step 2 may contain a fibroblast growth factor (FGF) receptor agonist. The FGF receptor (FGFR) agonist is a factor that binds to FGFR and acts on the intercellular signaling systems. The FGFR agonist may be an agonist of FGFR1, FGFR2, FGFR3, or FGFR4. The FGFR agonist includes human FGF, non-human FGF, and functionally modified derivatives thereof. The FGFR agonist is preferably FGF18 and more preferably human FGF18. The concentration of the FGFR agonist is 1 to 1000 ng/ml, preferably 5 to 500 ng/ml, more preferably 10 to 200 ng/ml, in particular 100 ng/ml. With the culture medium containing an FGFR agonist, integration of adjacent cartilaginous particles with one another can be promoted, resulting in promotion of plate-shaped cartilage formation.

The integration of cartilaginous particles begins with integration of the perichondrium-like membranes at the peripheries of the cartilaginous particles, followed by integration of the cartilages at the centers of the cartilaginous particles. The present inventor and others previously confirmed that FGF signaling promotes the integration of perichondrium-like membranes at an early stage of particle integration. Therefore, the culture medium containing an FGFR agonist is used temporarily at an early stage of step 2 and is not required to be used throughout the entire step 2. For example, the culture medium containing an FGFR agonist may be used within 28 days, 14 days, 12 days, 10 days, 9 days, 8 days, or 7 days after the start of step 2.

The culture temperature in step 2 is not particularly limited and is, for example, about 30 to 40° C., preferably about 37° C. The culture is performed under an atmosphere of air with $CO_2$. The $CO_2$ concentration is about 2 to 5%, preferably about 5%. The culture period in step 2 is not particularly limited as long as it is longer than a period of time required for adjacent cartilaginous particles to integrate with one another into a plate-shaped cartilage. The culture period in step 2 may be 7 days or more, 14 days or more, 21 days or more, 28 days or more, 35 days or more, 42 days or more, 49 days or more, 56 days or more, 63 days or more, or 70 days or more. The culture period in step 2 may be 140 days or less, 133 days or less, 126 days or less, 119 days or less, 112 days or less, 105 days or less, 98 days or less, 91 days or less, 84 days or less, 77 days or less, 70 days or less, 63 days or less, 56 days or less, 49 days or less, 42 days or less, 35 days or less, 28 days or less, 21 days or less, or 14 days or less. The formation of the plate-shaped cartilage can be confirmed by macroscopic observation of integration of adjacent cartilaginous particles with one another.

Pharmaceutical Composition

The present invention provides a pharmaceutical composition for cartilage injury repair, which composition comprises the plate-shaped cartilage of the present invention described above. The pharmaceutical composition of the present invention can comprise an effective amount of the plate-shaped cartilage of the present invention. The pharmaceutical composition as used herein can include pharmaceutical products, medical instruments, and regeneration medicine products. The administration method of the pharmaceutical composition of the present invention may be administration (transplantation) of the plate-shaped cartilage to a cartilage defect site in an injured cartilage. The plate-shaped cartilage is preferably administered after formed and optionally trimmed to fit the shape and size of the cartilage defect site. To the site of the contact between the defective cartilage and the plate-shaped cartilage, fibrin glue, gelatin gel, collagen gel, hyaluronan gel, or the like may be applied to prevent the plate-shaped cartilage from coming off. The plate-shaped cartilage after administration (transplantation) may be fixed with the periosteum or the like to the cartilage defect site. The plate-shaped cartilage may be fixed by suturing over the cartilage plate to the surrounding cartilage or bone. Examples of the subject suitable for administration of the pharmaceutical composition of the present invention include mammals (e.g., mice, rats, hamsters, rabbits, cats, dogs, cows, sheep, monkeys, humans). Preferred are humans.

Examples of the disease suitable for treatment with the pharmaceutical composition of the present invention include facial cartilage defects such as nasal and auricular cartilage defects; articular cartilage defects; meniscal tear and degeneration; and intervertebral disk or nucleus pulposus degeneration. Articular cartilage defects are, for example, traumatic cartilage injury and osteoarthritis. The pharmaceutical composition of the present invention may be used for prevention of the above-mentioned diseases.

The present invention also includes the following in addition to the pharmaceutical composition of the present invention.

(i) A cartilage repair method comprising the step of transplanting the plate-shaped cartilage of the present invention to a cartilage defect site.

(ii) The plate-shaped cartilage of the present invention for use in cartilage repair.

(iii) Use of the plate-shaped cartilage of the present invention for production of a pharmaceutical composition for injured cartilage repair.

The present invention further includes the following.

(1) A method for promoting integration of pluripotent stem cell-derived cartilages and/or integration of a pluripotent stem cell-derived cartilage and a native cartilage, the method comprising bringing a pluripotent stem cell-derived cartilage into contact with another pluripotent stem cell-derived cartilage and/or bringing a pluripotent stem cell-derived cartilage into contact with a native cartilage in the presence of a fibroblast growth factor (FGF) receptor agonist.

(2) The method according to the above (1), wherein the FGF receptor agonist is FGF18.

(3) A method for producing a cartilage mass for transplantation, the method comprising the step of culturing a plurality of pluripotent stem cell-derived cartilages in contact with one another in a culture medium containing an FGF receptor agonist.

(4) The method according to the above (3), wherein the FGF receptor agonist is FGF18.

(5) A cartilage mass for transplantation, comprising a plurality of pluripotent stem cell-derived cartilages integrated with one another.

(6) A cartilage repair method comprising the steps of: transplanting a pluripotent stem cell-derived cartilage to a cartilage defect site, and supplementing the transplantation site of the pluripotent stem cell-derived cartilage with an FGF receptor agonist.

(7) The method according to the above (6), wherein the FGF receptor agonist is FGF18.

(8) The method according to the above (6) or (7), wherein the method is for repairing an articular cartilage defect.

(9) The method according to the above (8), wherein the method is for repairing an articular cartilage defect in osteoarthritis.

EXAMPLES

Hereinafter, the present invention will be described in detail by examples, but the present invention is not limited thereto. All experiments were approved by the institutional review board, the institutional animal committee (as appropriate), and the institutional biosafety committee of Kyoto University.

Example 1

Integration of human iPS cell-derived cartilage particles in round-bottom 96-well plate 1. Materials and Methods (1) Cells Four human iPS cell lines, 409B2, 604B1, 1231A3, and QHJI, were gifted by K. Okita, M. Nakagawa, and S. Yamanaka from Center for iPS Cell Research and Application (CiRA), Kyoto University and used in this Example. 409B2 was generated from human dermal fibroblasts, and 604B1, 1231A3 and QHJI from human peripheral mononuclear cells. The cells were electroporated with episomal plasmid vectors (pCXLE-hOCT3/4-shp53-F, hSK, hUL, EBNA1). No genomic integration of the transgenes was detected.

(2) Production of Human iPS Cell-Derived Cartilaginous particles

Human iPS cell-derived cartilaginous particles (hereinafter referred to as "cartilaginous particles") were produced according to a modified version of the method described in Non Patent Literature 1. The specific procedure was as follows.

(2-1) Culture of Human iPS Cells

The human iPS cells in culture were incubated with 0.5× TrypLE Select and then detached using a cell scraper. After cell counting, $0.5\times10^7$ to $1.0\times10^7$ cells were transferred to a 100-mL bioreactor (BWV-S10A, ABLE Corporation). To the bioreactor, 100 mL of StemFit AK03N (Ajinomoto) supplemented with 10 nM Y-27632 (Wako) was added, and the cells were cultured under the conditions of 37° C. and 5% $CO_2$ for 4 to 7 days with stirring using a magnetic stirrer (BWS-S03NOS-6, ABLE Corporation) rotating at 60 rpm. As a result, iPS cell clusters of 50 to 300 μm in diameter were obtained.

(2-2) Chondrogenic Induction

The iPS cell clusters obtained as above were collected and seeded on four to twelve 10-cm suspension culture dishes (Sumitomo) with 5 mL of chondrogenic differentiation medium. The chondrogenic differentiation medium used was DMEM (SIGMA) supplemented with 0.2% FBS (Invitrogen), 1% ITS-λ (Invitrogen), 50 μg/mL ascorbic acid (Nakalai), $1\times10^{-4}$ M non-essential amino acids (Invitrogen), 1 mM sodium pyruvate (Invitrogen), 10 ng/ml BMP2 (PeproTech), 10 ng/ml TGF-β3 (Wako), 10 ng/ml GDF5 (Biovision), and 1 μM rosuvastatin (Biovision). After seeding, the iPS cell clusters were cultured under the conditions of 37° C. and 5% $CO_2$. After 1 to 3 days, the chondrogenic differentiation medium was changed to a fresh one. Afterwards, medium change was performed at intervals of 2 to 5 days during 2 to 3 weeks of culture. During the culture period, the iPS cell clusters gradually adhered on the dishes and ultimately formed nodules. Some of the nodules were in a suspended state after spontaneous detachment from the dishes, and the remaining adherent nodules were detached using a cell scraper. The nodules were transferred to 6-cm suspension culture dishes (Sumitomo) and cultured under the conditions of 37° C. and 5% $CO_2$. After 1 to 5 days, the chondrogenic differentiation medium was changed to a fresh one. Afterwards, medium change was performed every 2 to 7 days. At the time of medium change, if there were nodules stuck to the dish, they were detached using a cell scraper and suspended in the medium. Cartilaginous particles at 12 weeks after the start of the chondrogenic induction were used for the following experiments.

(3) In Vitro Integration of Cartilaginous Particles

Two cartilaginous particles were put into a well of a round-bottom 96-well plate (see FIGS. 1A and 1B) and cultured under the conditions of 37° C. and 5% $CO_2$ in chondrogenic medium (DMEM (Sigma) with 1% ITS, 1% FBS, 2 mM L-glutamine (Thermo), $1\times10^{-4}$ M non-essential amino acids (Thermo), 1 mM sodium pyruvate (Thermo), 50 U of penicillin, 50 mg/mL streptomycin, 50 μg/mL ascorbic acid (Nacalai), 10 ng/mL BMP2 (Peprotech), 10 ng/ML TGFβ1 (Peprotech), and 10 ng/ML GDF5 (PTT)). In total, 84 wells, each of which contained a pair of cartilaginous particles, were prepared. The wells were divided into 7 groups (12 pairs per group), and each was subjected to macroscopic and histological analyses at the predetermined time points (0, 3, 7, 14, 28, or 56 days after the start of the integration experiment). The medium was changed every day gently and carefully so as not to change the positions of the cartilaginous particles.

(4) Time-Lapse Imaging of Integration

Cartilaginous particles were prepared from a human iPS cell line 201B7 bearing a CAG-EGFP (317-12) or CAG-mCherry (511-5B) transgene targeted to the AAVS1 locus. The process of integration of an EGFP cartilaginous particle and an mCherry cartilaginous particle was time-lapse recorded using a multiphoton laser microscope (Nikon A1R MP+) and an analysis software (Nikon NIS Elements). Fluorescent images were captured every 1 h for 11.5 consecutive days. Each image in the movie represents 100 ms; thus 24 h corresponds to 2.4 s. The time-lapse imaging was interrupted several times when the iPS-derived cartilaginous particles moved out of the field of view.

(5) Examination of FGF Signaling During Integration of Cartilaginous Particles

Recombinant human FGF18 (PeproTech) was dissolved in phosphate-buffered saline (PBS) to prepare a stock solution (100 μg/mL). In total, 90 pairs of cartilaginous particles were cultured under the conditions described in the above (3). One pair per well was cultured in 0.3 mL of medium. Forty-five pairs were cultured in a medium supplemented with vehicle (0.3 μL of PBS), and the other 45 pairs were cultured in a medium supplemented with 0.3 μL of the FGF18 stock solution (final concentration: 100 ng/mL). The 45 pairs in each treatment group were further separated into three equal-sized groups and subjected to histological analysis (3, 7, or 14 days after the start of the experiment).

To further investigate the effects of FGF on the integration, an EGFR inhibitor, NVP-BGJ398 (ChemScene LLC), was used in the culture. NVP-BGJ398 was dissolved in DMSO to prepare a 50 μM stock solution. In total, 30 new pairs of cartilaginous particles were cultured under the conditions described in the above (3). Fifteen pairs were cultured in a medium supplemented with vehicle (0.3 μL of DMSO), and the other 15 pairs were cultured in a medium supplemented with 0.3 μL of the NVP-BGJ398 stock solution (final concentration: 50 nM). After 14 days of culture, the samples were subjected to histological analysis.

(6) Histological Analysis

The pairs of cartilaginous particles were fixed with 4% paraformaldehyde, processed, and embedded in paraffin. 20 to 150 serial sections were prepared around the integrated portion of the sample so that the sections contain the most contact area between the paired cartilaginous particles (see FIG. 1C). Serial sections with the greatest contact portion were selected and used for further analysis. The sections were stained with hematoxylin-eosin and safranin O-fast green-iron hematoxylin and immunostained with a goat anti-type I collagen antibody (Souther Biotech) and an anti-type II collagen antibody (Thermo).

(7) RNA Extraction

Cartilaginous particles were prepared from the human iPS cell line QHJI, and the perichondrium-like membrane of the cartilaginous particle was peeled off using forceps under a stereomicroscope to separate the perichondrium-like membrane from the central cartilage. The perichondrium-like membrane and the central cartilage were separately subjected to RNA extraction. More specifically, the samples were frozen in liquid nitrogen and crushed using Multi Beads Shocker (Yasui Kikai), and total RNAs were extracted using ISOGEN (registered trademark) (Nippon Gene) and purified with RNeasy (registered trademark) (Qiagen).

(8) RNA Sequencing Analysis

The quality of the extracted RNAs was evaluated using Bioanalyzer 2100 (Agilent Technologies). One microgram of the total RNA was subjected to library preparation using TruSeq (registered trademark) Stranded mRNA Library Prep Kit (Illumina) according to the manufacturer's instruction. The quality and quantity of the constructed libraries were evaluated using Bioanalyzer 2100 and Qubit (registered trademark) dsDNA HS assay kit (Thermo). The libraries were sequenced in 75-cycle single-read mode of NextSeq (registered trademark) 500 (Illumina). All sequence reads were extracted in FASTQ format using BCL2FASTQ Conversion Software (v2.17.1.14). The adaptors, the poly-A sequences, and the low-quality bases at the 3' read ends were trimmed using cutadapt-1.12. Untrimmed and trimmed reads were mapped onto the human genome hg38 using TopHat-2.1.1. The human gene annotation from the GENCODE release v25 was utilized. For gene expression analysis, the expression level of each gene was normalized to reads per kilobase of exon per million sequence reads (RPKM) using Cufflinks-2.2.1.

(9) Real-Time RT-PCR Expression Analysis

Total RNAs were extracted separately from three perichondrium-like membrane samples, three central cartilage samples, and three whole cartilaginous particles. Five hundred nanograms of the total RNA was reverse-transcribed into first-strand cDNA using ReverTra Ace (registered trademark)

(Toyobo, Tokyo, Japan) and an oligo (dT) 20 primer. PCR amplification was performed using KAPA PROBE FAST qPCR kit or KAPA SYBR (registered trademark) FAST qPCR kit Master Mix ABI prism (KAPA Biosystems, MA, USA). The PCR primers used are listed in Table 1. The RNA expression levels were normalized to that of GAPDH. Amplified products were used to derive standard curves for real-time quantitative RT-PCR.

TABLE 1

| Primer | Sequence or TagMan ID |
|---|---|
| FGP18 forward | CACTTTCTACTGCTGCTGCTTCCA (SEQ ID NO: 1) |
| FGF18 reverse | GCATACTTGTCCCCGTCCTC (SEQ ID NO: 2) |
| COL1A1 | Hs00164004_m1 |
| COL2A1 | Hs00264051_m1 |
| SOX9 | Hs01001343_g1 |
| GAPDH | Hs03929097_g1 |

(10) Statistical Analysis

The data are shown as means and standard deviations. In this study, the two-tailed Student's t-test or the Steel-Dwass test was used. P-values <0.05 were considered to be statistically significant.

Figure 2:
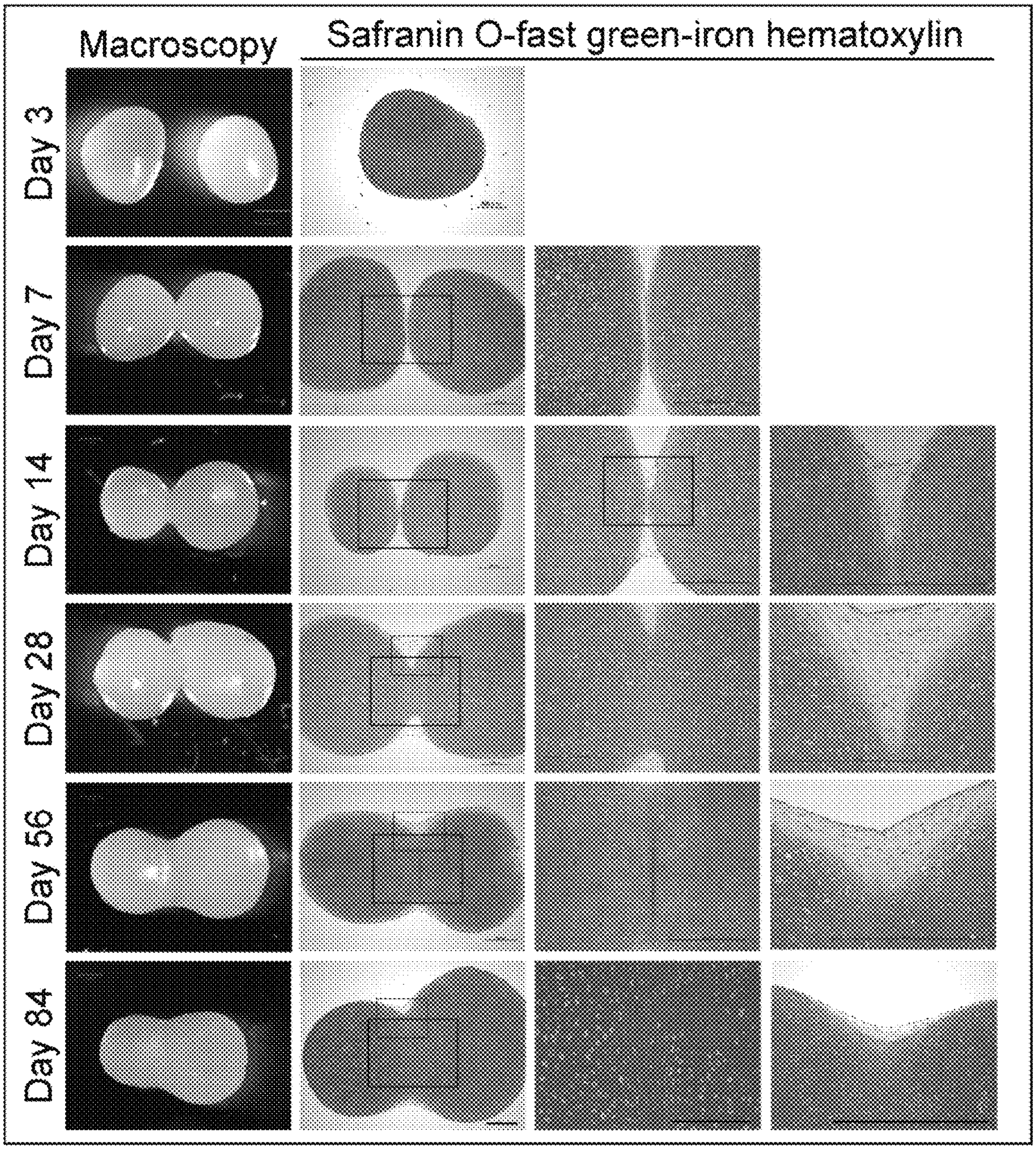
FIG. 2 shows a pair of human iPS cell line QHJI-derived cartilaginous particles in a round-bottom 96-well plate observed after 3, 7, 14, 28, 56, and 84 days of culture. The left column shows macroscopic images of the pair of QHJI-derived cartilaginous particles. The second column shows images of histological sections stained with safranin O-fast green-iron hematoxylin. The third column shows enlarged views of the boxed regions in the second column. The right column shows enlarged views of the boxed regions in the second and third columns. Scale bars mark 500 μm.

2. Results (1) Analysis of the Process of In Vitro Integration Between QHJI Cartilaginous Particles Two cartilaginous particles started to bond to each other after 7 days and then gradually form a solid union (FIG. 2, left column). Histologically, one cartilaginous particle consists of cartilage at the center and perichondrium-like membranous tissue that wraps around the cartilage (FIG. 2, second and third columns, and right column). On day 7, when the cartilaginous particles started to integrate with each other, only the perichondrium-like membranes were integrated, whereas the cartilages of the cartilaginous particles were still separated by the membrane. A portion of the perichondrium-like membrane at the integrated site was thickened on days 14, 28, and 56 (FIG. 2, right column), indicating that the cells in the perichondrium-like membrane had proliferated. On day 14, the cartilages of the two cartilaginous particles were in partial contact. The contact was more substantial on day 28, and the cartilages were integrated before days 56 and 84 (FIG. 2, second and third columns).

Figure 3:
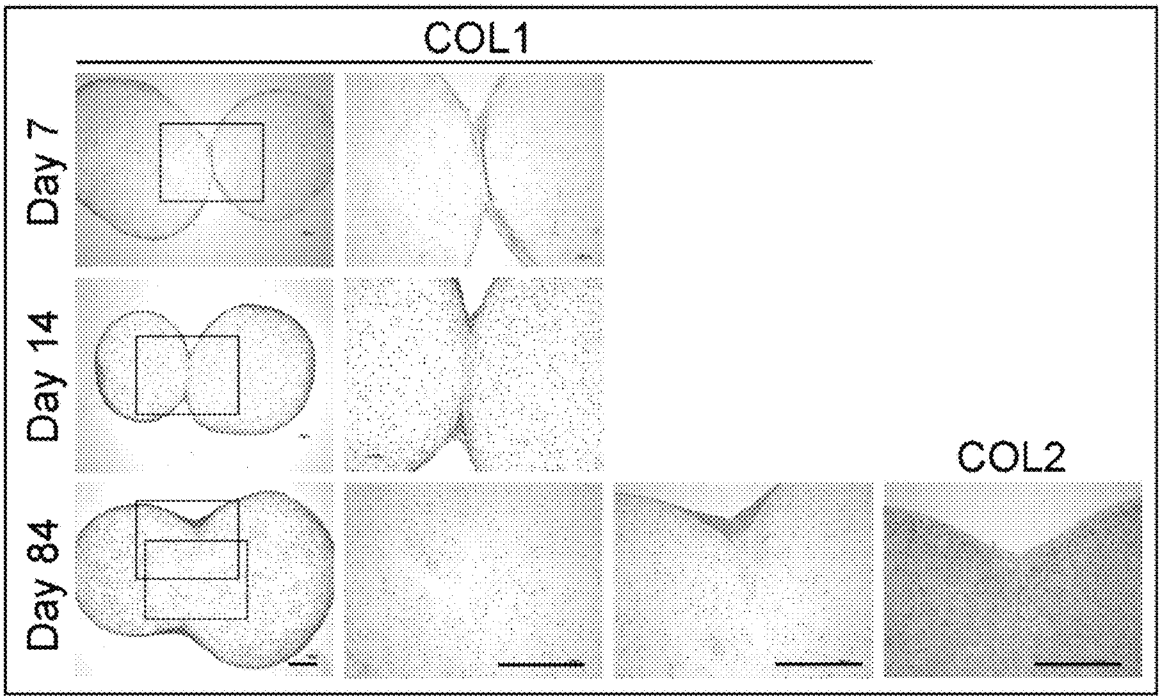
FIG. 3 shows anti-type I collagen antibody-immunostained sections of the integrated cartilaginous particles after 7, 14, and 84 days of culture of a pair of human iPS cell line QHJI-derived cartilaginous particles in a round-bottom 96-well plate (left column, second column, and third column); and an anti-type II collagen antibody-immunostained section of the integrated cartilaginous particles after 84 days of culture. The second and third columns show enlarged views of the boxed regions in the left column. Scale bars mark 500 μm.

The perichondrium-like membrane in the cartilaginous particles expressed type I collagen (FIG. 3). On the other hand, the central cartilage expressed type II collagen (FIG. 3, right column). On day 7, a clear line indicative of type I collagen expression was observed in the contact face between the two cartilaginous particles (FIG. 3, second column), indicating that the contact was formed between the perichondrium-like membranes. On day 14, the type I collagen-expressing line was disappearing, and it completely disappeared by day 84, indicating that the cartilages of the two cartilaginous particles were integrated. Type II collagen was expressed in the connected site as strongly as it was in the central cartilage (FIG. 3, right column).

(2) Statistical Analysis of Integration Progression of Cartilaginous Particles

For statistical analysis, the degree of integration of cartilaginous particles at each time point was graded as follows: grade 0, no integration; grade 1, perichondrium-like membrane integration; grade 2, cartilage integration (Table 2). The grades are non-parametric data, and statistical analysis was performed using the Steel-Dwass test. All the samples were graded as 0 (no integration) on day 0 and graded as 2 (cartilage integration) on day 56. The grades on the time points after day 7 were significantly different from those on day 0 (Table 3). The grades on the time points before day 14 were significantly different from those on day 56 (Table 3).

TABLE 2

| | Grade 0 No integration | Grade 1 Integration by perichondrium-like membrane | Grade2 Integration by cartilage | Total |
|---|---|---|---|---|
| Day 0 | 12 | 0 | 0 | 12 |
| Day 3 | 12 | 0 | 0 | 12 |
| Day 7 | 5 | 7 | 0 | 12 |
| Day 10 | 2 | 9 | 1 | 12 |
| Day 14 | 0 | 8 | 4 | 12 |
| Day 28 | 0 | 5 | 7 | 12 |
| Day 56 | 0 | 0 | 12 | 12 |

TABLE 3

Table 3. Statistical analysis of Table 2

| | Day 0 | Day 3 | Day 7 | Day 10 | Day 14 | Day 28 | Day 56 |
|---|---|---|---|---|---|---|---|
| Day 0 | | | | | | | |
| Day 3 | N.S. | | | | | | |
| Day 7 | * | * | | | | | |
| Day 10 | ** | ** | N.S. | | | | |
| Day 14 | ** | ** | * | N.S. | | | |
| Day 28 | ** | ** | ** | N.S. | N.S. | | |
| Day 56 | ** | ** | ** | ** | ** | N.S. | |

Figure 4:
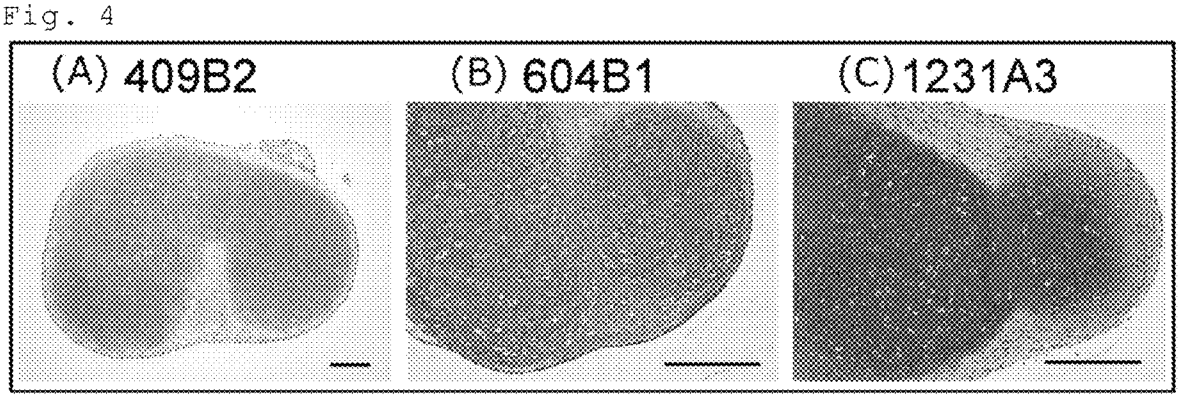
FIG. 4 shows safranin O-fast green-iron hematoxylin-stained sections of the integrated cartilaginous particles after 60 days of culture of a pair of human iPS cell line-derived cartilaginous particles in contact with each other in a culture dish. Three human iPS cell lines 409B2, 604B1, and 1231A3 were used.

*P < 0.05 and **P < 0.01 by Steel-Dwass test.
N.S., Not significant (3) Integration of Cartilaginous Particles Derived from Other Human iPS Cell Lines To examine whether cartilaginous particles derived from human iPS cell lines other than QHJI could integrate, cartilaginous particles were produced from human iPS cell lines 409B2, 604B1, and 1231A3. Two cartilaginous particles were cultured under adherent conditions on a culture dish. During the culture, the cartilaginous particles spontaneously and gradually integrated with each other. This cartilaginous particle integration was histologically confirmed by safranin O-fast green-iron hematoxylin staining of sections on day 60 (FIG. 4).

(4) Time-Lapse Imaging of Cartilaginous Particle Integration

Time-lapse imaging of the cartilaginous particle integration indicated that cells in the perichondrium-like membrane migrated into the perichondrium-like membrane of the other cartilaginous particle. This observation suggests that the perichondrium-like membrane plays a substantial role during cartilaginous particle integration.

Figure 5:
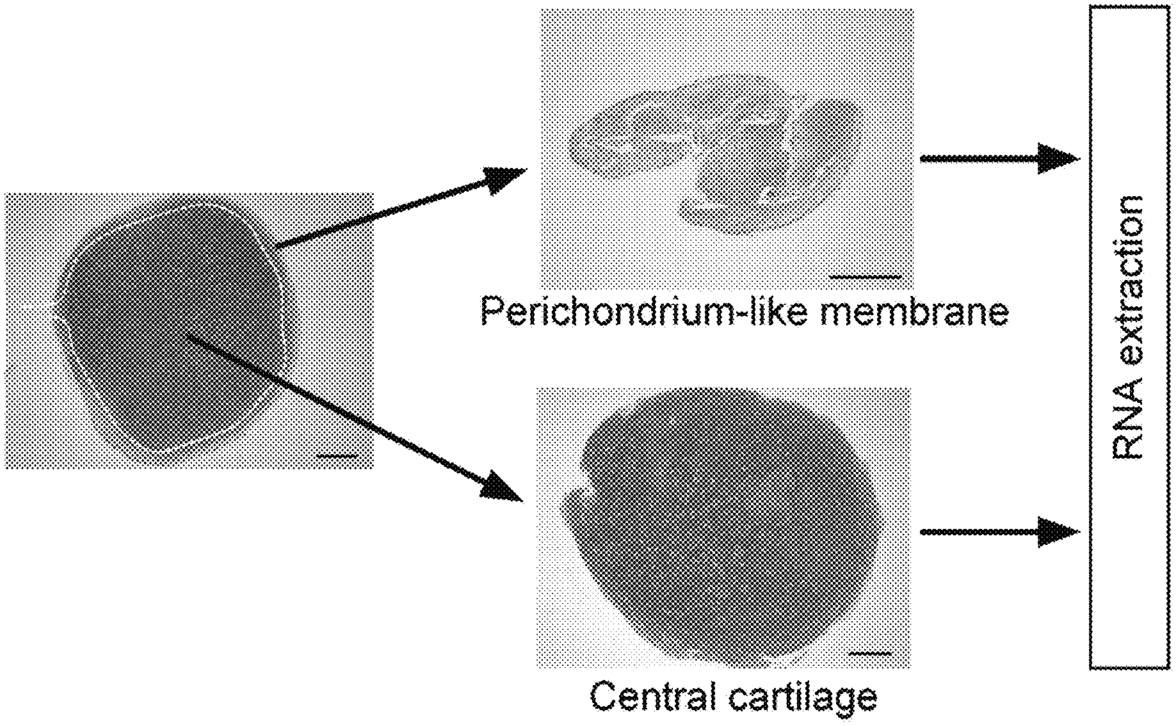
FIG. 5 shows safranin O-fast green-iron hematoxylin-stained sections of a perichondrium-like membrane (upper right) and a central cartilage (lower right) separated from a cartilaginous particle before integration (left).
Figure 6:
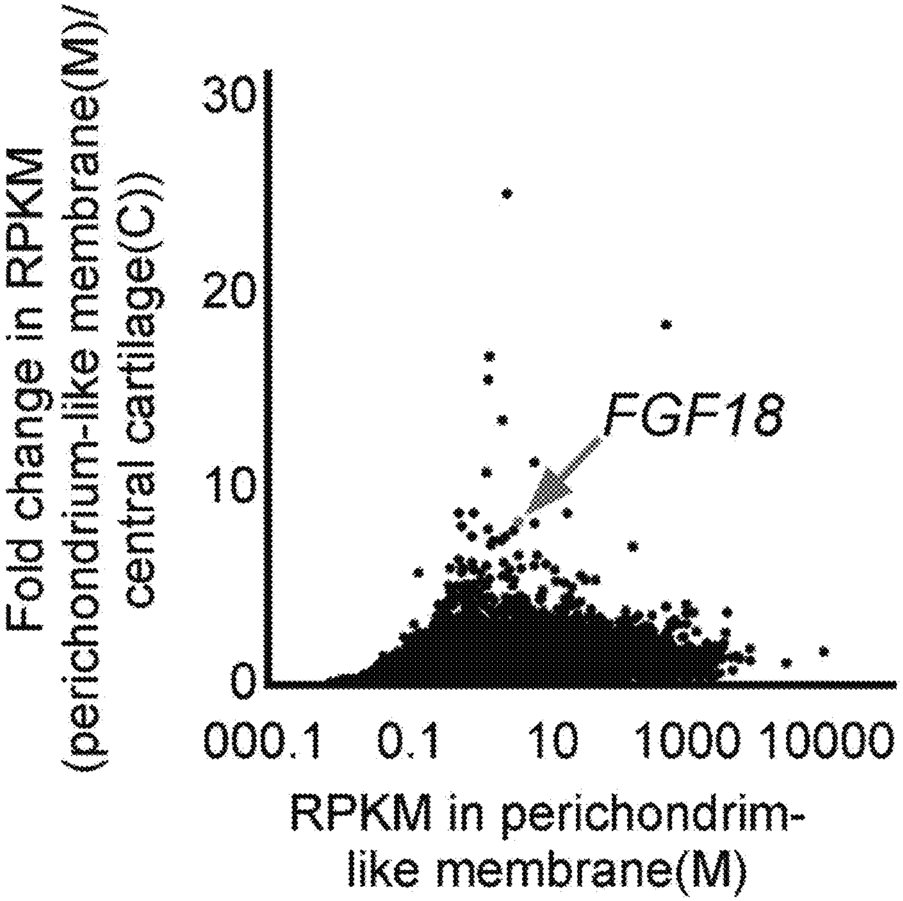
FIG. 6 is a plot showing gene expression difference between the perichondrium-like membrane and the central cartilage. Each dot represents one gene. The y-axis represents the fold change in the RPKM in the perichondrium-like membrane versus that in the central cartilage. The x-axis represents the log 10 of the RPKM in the perichondrium-like membrane. The arrow indicates the FGF18 gene.
Figure 7:
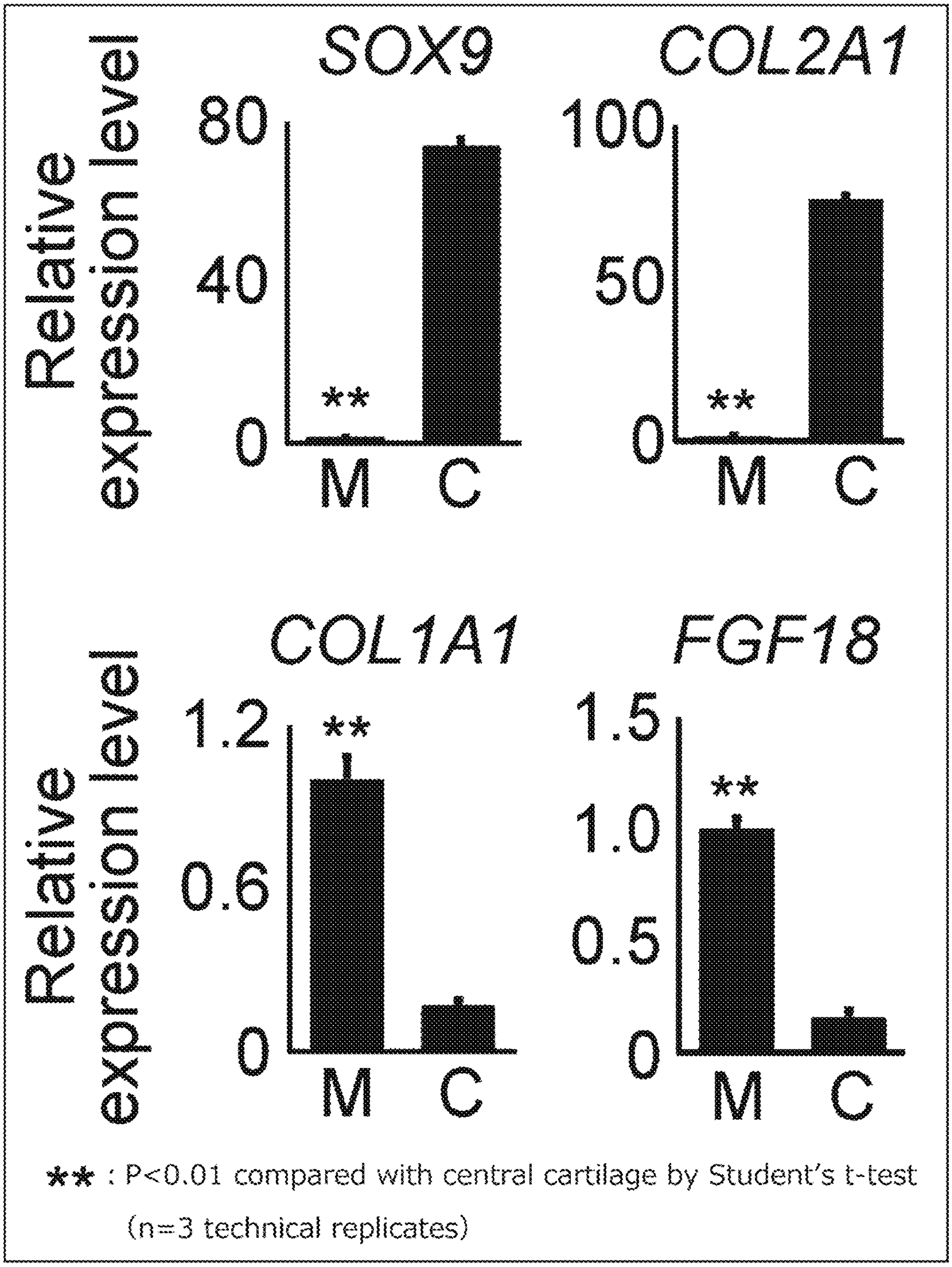
FIG. 7 shows the results of real-time RT-PCR expression analysis of marker genes in the perichondrium-like membrane and the central cartilage. M stands for the perichondrium-like membrane, and C stands for the central cartilage. Error bars denote means±standard deviations.

(5) mRNA Expression Analysis of Perichondrium-Like Membrane of Cartilaginous Particles Histological analysis of dissected samples confirmed separation between the perichondrium-like membrane and the central cartilage (FIG. 5). RNAs were extracted separately from the perichondrium-like membrane and the central cartilage and subjected to RNA sequencing analysis. The RPKM values for COL2A1 and Sox9 were higher in the central cartilage than in the perichondrium-like membrane, whereas the RPKM values for COL1A1 were vice versa (Table 4). These results show that the sampling and RNA sequencing experiments were properly performed. Among differentially expressed genes, FGF18 mRNA was expressed more highly in the perichondrium-like membrane than in the central cartilage (Tables 4 and 5, and FIG. 6). The real-time RT-PCR expression analysis confirmed that the four genes were differentially expressed between the perichondrium-like membrane and the central cartilage (FIG. 7).

TABLE 4

| | RPKM | | |
|---|---|---|---|
| GENE | Perichondrium-like Membrane (M) | Central Cartilage (C) | M/C |
| SOX9 | 4.75 | 39.27 | 0.12 |
| COL2A1 | 200.95 | 6223.85 | 0.03 |
| COL1A1 | 628.33 | 282.44 | 2.23 |
| FGF18 | 3.48 | 0.42 | 8.29 |

TABLE 5

| | RPKM | | |
|---|---|---|---|
| GENE | Perichondrium-like Membrane (M) | Central Cartilage (C) | M/C |
| CHST9 | 2.24 | 0.09 | 25.07 |
| CHI3L1 | 397.46 | 21.62 | 18.38 |
| POLM | 1.27 | 0.08 | 16.76 |
| GGT7 | 1.17 | 0.08 | 15.58 |
| WISP2 | 1.90 | 0.14 | 13.46 |
| NRN1 | 5.45 | 0.48 | 11.29 |
| SLC22A1 | 1.12 | 0.10 | 10.79 |
| ZNF354C | 0.73 | 0.08 | 8.74 |
| C2orf91 | 0.47 | 0.05 | 8.74 |
| ADAMTSL1 | 15.90 | 1.82 | 8.72 |
| FGF18 | 3.48 | 0.42 | 8.19 |
| CD70 | 5.34 | 0.65 | 8.18 |
| NELL1 | 0.51 | 0.06 | 8.03 |
| CD74 | 1.20 | 0.15 | 7.86 |
| C3 | 2.75 | 0.35 | 7.84 |

(6) FGF18-Mediated Regulation of Cartilaginous Particle Integration

Figure 8:
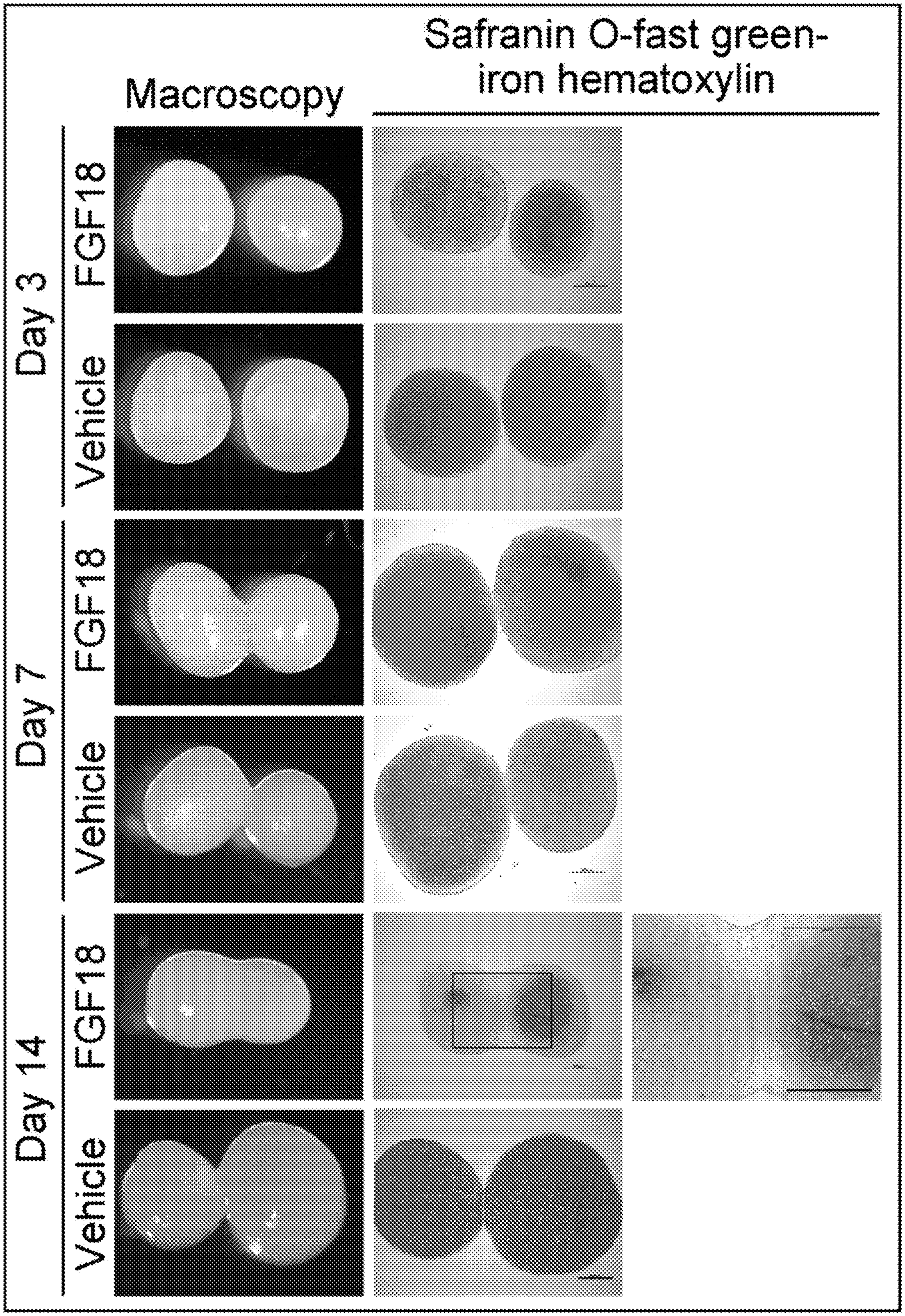
FIG. 8 shows pairs of human iPS cell line QHJI-derived cartilaginous particles observed after 3, 7, and 14 days of culture in the presence of FGF18 (final concentration: 100 ng/mL) or vehicle in a round-bottom 96-well plate. The left column shows macroscopic images of the pairs of QHJI-derived cartilaginous particles. The second column shows images of histological sections stained with safranin O-fast green-iron hematoxylin. The third column shows an enlarged view of the boxed region in the second column. Scale bars mark 500 μm.

The addition of FGF18 to the medium accelerated the integration of cartilaginous particles. On day 14, vehicle-treated cartilaginous particles showed minimal integration, whereas FGF18-treated cartilaginous particles showed substantial integration (FIG. 8). Histologically, FGF18-treated cartilaginous particles showed a thick connection of the perichondrium-like membranes. Significant difference was observed in the integration grade between the vehicle-treated and FGF18-treated pairs of cartilaginous particles on day 14 (Table 6).

TABLE 6

| | | Grade 0 No integration | Grade 1 Integration by perichondrium-like membrane | Grade2 Integration by cartilage | Total |
|---|---|---|---|---|---|
| Day | Vehicle | 14 | 1 | 0 | 15 |
| 3 | FGF18 | 12 | 3 | 0 | 15 |
| Day | Vehicle | 12 | 3 | 0 | 15 |
| 7 | FGF18 | 10 | 5 | 0 | 15 |
| Day | Vehicle | 9 | 5 | 1 | 15 |
| 14 | FGF18 ** | 1 | 14 | 0 | 15 |

** $P < 0.01$ compared with Vehicle by the Steel-Dwass test.

Figure 9:
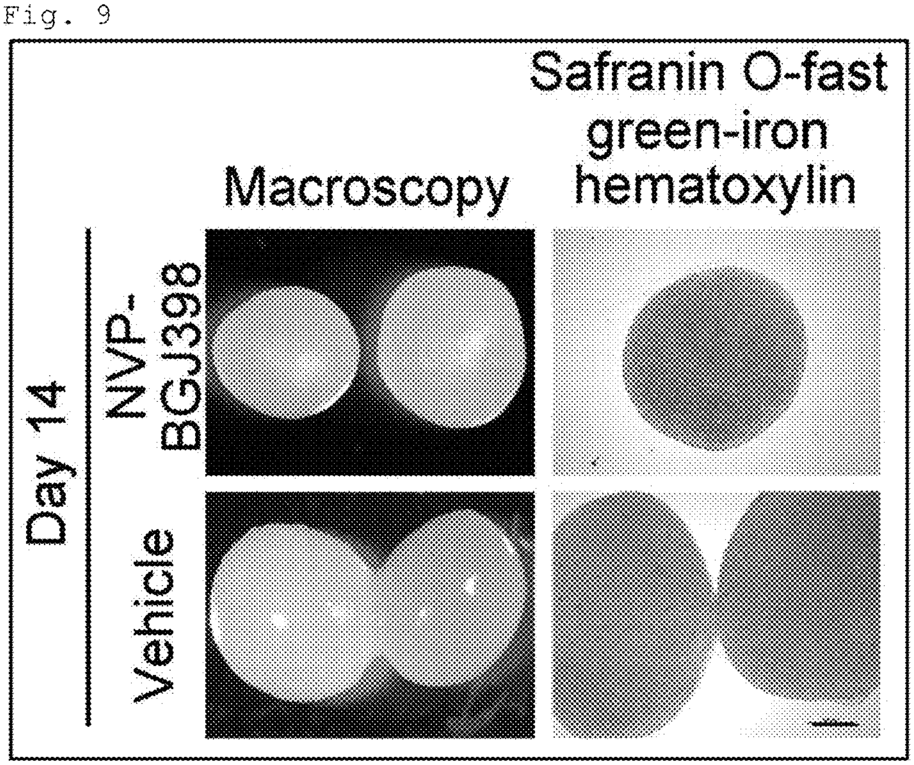
FIG. 9 shows pairs of human iPS cell line QHJI-derived cartilaginous particles observed after 14 days of culture in the presence of the FGFR inhibitor NVP-BGJ398 (final concentration: 50 nM) or vehicle in a round-bottom 96-well plate. The left column shows macroscopic images of the pairs of QHJI-derived cartilaginous particles. The second column shows images of histological sections stained with safranin O-fast green-iron hematoxylin. Scale bars mark 500 μm.

In contrast, the addition of the FGFR inhibitor NVP-BGJ398 to the medium inhibited the integration of cartilaginous particles. On day 14, 11 out of 15 pairs of vehicle-treated cartilaginous particles showed integration, whereas no pairs of NVP-BGJ398-treated cartilaginous particles showed integration (FIG. 9 and Table 7).

TABLE 7

| | | Grade 0 No integration | Grade 1 Integration by perichondrium-like membrane | Grade2 Integration by cartilage | Total |
|---|---|---|---|---|---|
| Day | Vehicle | 4 | 5 | 6 | 15 |
| 14 | NVP-BGJ398 ** | 15 | 0 | 0 | 15 |

** $P < 0.01$ compared with Vehicle by the Steel-Dwass test.

Example 2

Integration of Human iPS Cell-Derived Cartilaginous Particles in Mesh Bag

Figure 10:
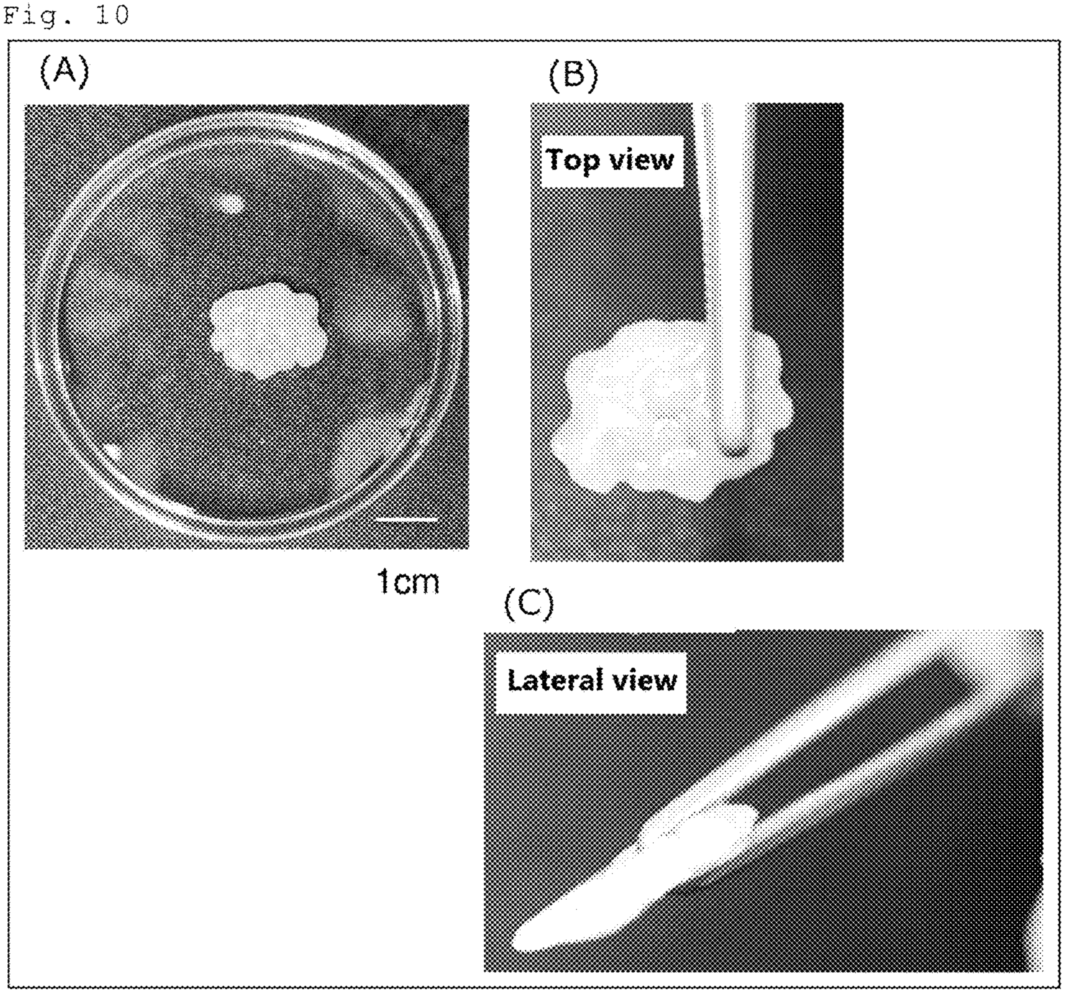
FIG. 10A shows images of a plate-shaped cartilage obtained after 4 weeks of culture of human iPS cell-derived cartilaginous particles in a mesh bag in a stirred bioreactor with chondrogenic medium.
FIG. 10B is an enlarged top view.
FIG. 10C is an enlarged lateral view.
Figure 11:
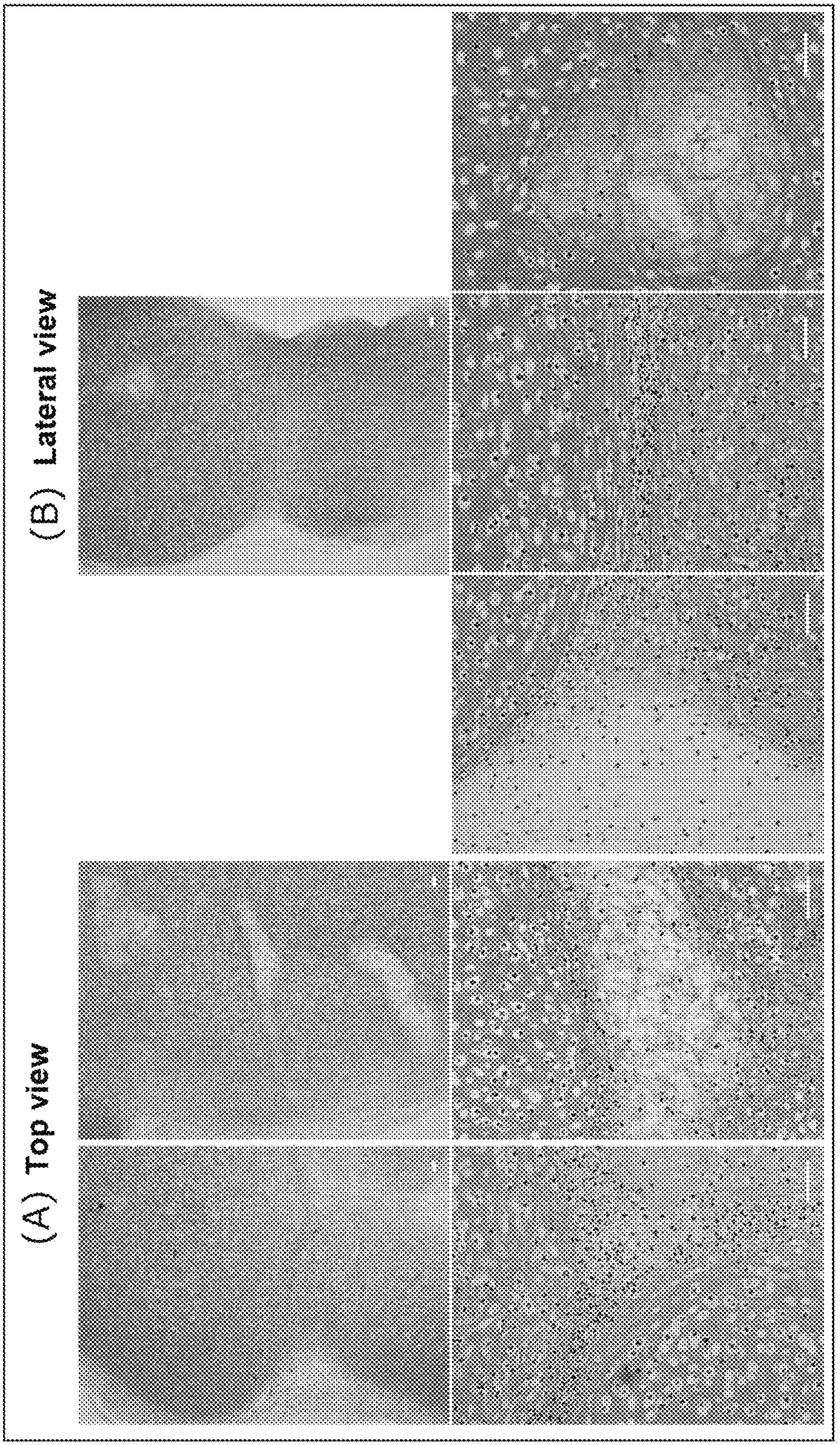
FIG. 11 shows images of safranin O-fast green-iron hematoxylin-stained sections of the plate-shaped cartilage of FIG. 10.

Cartilaginous particles were produced from the human iPS cell line QHJI in the same manner as in Section (2) of "Materials and methods" in Example 1. The cartilaginous particles at 4 weeks after the start of the differentiation were used in this example. The cartilaginous particles were placed into a mesh bag for biopsy sample storage (EIKEN CHEMICAL, trade name: Sample bag, product number: KA1000, 45 mm×74 mm). The amount of the cartilaginous particles in the mesh bag was an amount corresponding to 30% to 40% of the total area (30 mm×50 mm) of the mesh bag tilted such that the cartilaginous particles collected into one corner of the mesh bag. The mesh bag containing the cartilaginous particles was placed into a bioreactor (BWV-S03A, ABLE) containing the chondrogenic medium described in Section (3) of "Materials and methods" in Example 1. Culture was performed under the conditions of 37° C. and 5% $CO_2$ with stirring of the medium for 4 weeks. The cartilaginous particles taken from the mesh bag were in the form of a plate-shaped cartilage (FIG. 10). FIG. 11 shows safranin O-fast green-iron hematoxylin-stained images of histological sections of the obtained plate-shaped cartilage. The histological images show that cells are dispersed in safranin O-stained cartilage ECM, which is distinctive of cartilage.

Example 3

Integration of Human iPS Cell-Derived Cartilaginous Particles in Frame

Figure 12:
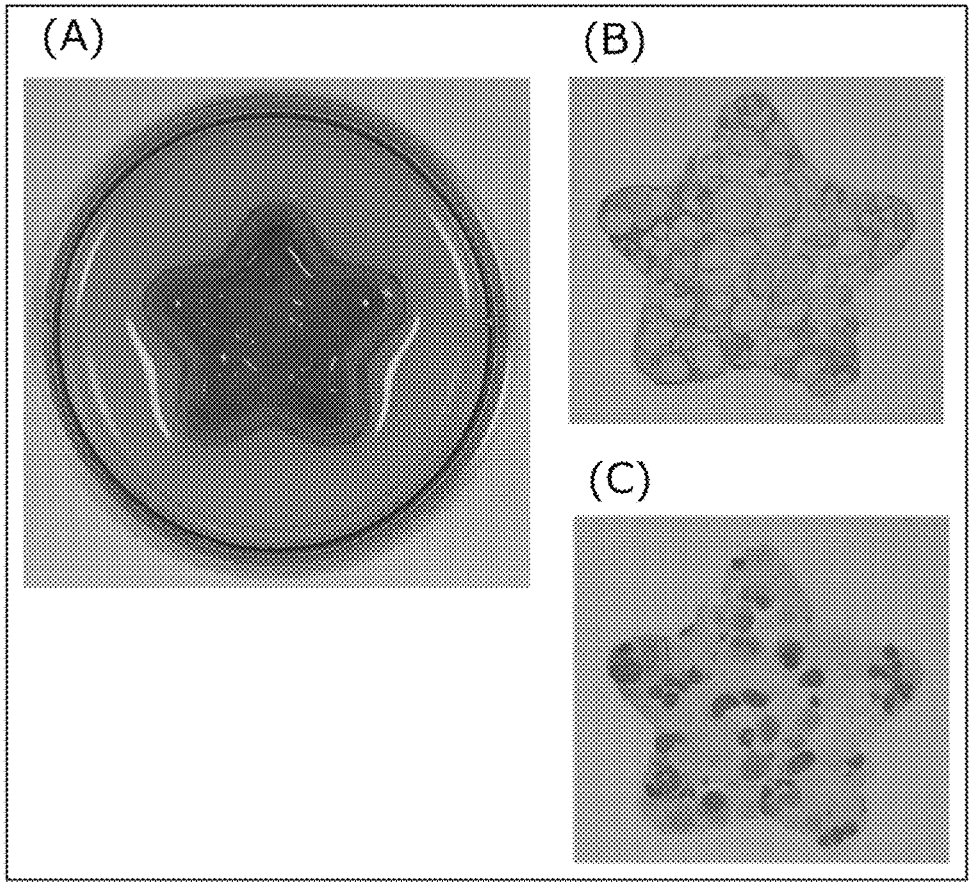
FIG. 12A shows images of a star-shaped, plate-shaped cartilage obtained after 4 weeks of culture of human iPS cell-derived cartilaginous particles in a star-shaped frame placed on a culture dish with chondrogenic medium.
FIG. 12B is an image of a hematoxylin eosin-stained section of the plate-shaped cartilage.
FIG. 12C is an image of a safranin O-fast green-iron hematoxylin-stained section of the plate-shaped cartilage.

Cartilaginous particles were produced from the human iPS cell line 409B2 in the same manner as in Section (2) of "Materials and methods" in Example 1. Rosuvastatin was not used in this example. The cartilaginous particles at 8 weeks after the start of the differentiation were used in this example. The chondrogenic medium described in Section (3) of "Materials and methods" in Example 1 was placed into a 3.5-cm culture dish, and a star-shaped frame was placed on the dish. The cartilaginous particles were placed in the frame without any space among the particles, and the culture dish was kept under the conditions of 37° C. and 5% $CO_2$ for 16 weeks of culture. The cartilaginous particles in the frame formed a star-shaped, plate-shaped cartilage (FIG. 12).

Example 4

Integration of Human iPS Cell-Derived Cartilaginous Particles in Transwell

Figure 13:
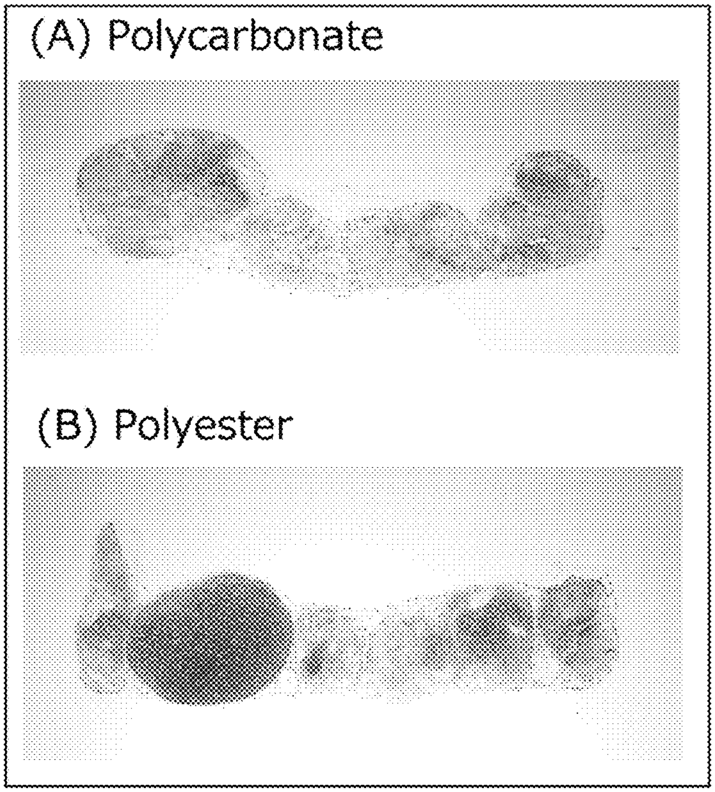
FIG. 13 shows integrated cartilage obtained after 4 weeks of culture of human iPS cell-derived cartilaginous particles in a polyester or polycarbonate transwell placed in a well of a 24-well plate with chondrogenic medium.

Cartilaginous particles were produced from the human iPS cell line QHJI in the same manner as in Section (2) of "Materials and methods" in Example 1. The cartilaginous particles at 4 weeks after the start of the differentiation were used in this example. A polycarbonate or polyester transwell was used in this example. The chondrogenic medium described in Section (3) of "Materials and methods" in Example 1 was placed into each well of a 24-well plate (Corning), and a transwell (membrane diameter: 6.5 mm) was placed in each well. The cartilaginous particles were placed in the transwell without any space among the particles, and the plate was kept under the conditions of 37° C. and 5% $CO_2$ for 5 weeks of culture. The cartilaginous particles in the transwell were integrated in the form of a plate-shaped cartilage (FIG. 13).

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A method for producing a pluripotent stem cell-derived cartilage comprising a layer of a plurality of pluripotent stem cell-derived cartilaginous particles consisting of pluripotent stem cell-derived chondrocytes, cartilage extracellular matrix produced by the chondrocytes, and perichondrium-like membranes, said method comprising;

step 1: producing pluripotent stem cell-derived cartilaginous particles by inducing pluripotent stem cells to differentiate into the chondrocytes and to produce the cartilage extracellular matrix, and step 2: culturing the pluripotent stem cell-derived cartilaginous particles contained in a liquid-permeable vessel in a culture medium, wherein adjacent pluripotent stem cell-derived cartilaginous particles integrate in contact with one another thereby forming said layer, wherein the culturing is performed in culture medium under flow conditions.

2. The method according to claim 1, wherein the culture medium comprises FGF18.

* * * * *

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
```

-continued

```
<220> FEATURE:
<223> OTHER INFORMATION: Primer

<400> SEQUENCE: 1

cactttctac tgctgctgct tcca                                    24


<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2

gcatacttgt ccccgtcctc                                         20
```